(12) United States Patent
Katsuki

(10) Patent No.: US 10,855,980 B2
(45) Date of Patent: Dec. 1, 2020

(54) MEDICAL-IMAGE DISPLAY CONTROL DEVICE, MEDICAL IMAGE DISPLAY DEVICE, MEDICAL-INFORMATION PROCESSING SYSTEM, AND MEDICAL-IMAGE DISPLAY CONTROL METHOD

(71) Applicant: Sony Olympus Medical Solutions Inc., Tokyo (JP)

(72) Inventor: Shinji Katsuki, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/481,064

(22) PCT Filed: Oct. 27, 2017

(86) PCT No.: PCT/JP2017/038920
§ 371 (c)(1),
(2) Date: Jul. 25, 2019

(87) PCT Pub. No.: WO2018/163499
PCT Pub. Date: Sep. 13, 2018

(65) Prior Publication Data
US 2019/0394454 A1 Dec. 26, 2019

(30) Foreign Application Priority Data
Mar. 10, 2017 (JP) .................................. 2017-046099

(51) Int. Cl.
*A61B 90/00* (2016.01)
*H04N 13/385* (2018.01)
*H04N 13/398* (2018.01)

(52) U.S. Cl.
CPC ........... *H04N 13/398* (2018.05); *A61B 90/37* (2016.02); *H04N 13/385* (2018.05); *A61B 2090/372* (2016.02)

(58) Field of Classification Search
CPC .................................................... H04N 13/398
See application file for complete search history.

(56) References Cited

U.S. PATENT DOCUMENTS 6,122,000 A * 9/2000 Yee ...................... H04N 13/341
348/51
8,463,022 B2 * 6/2013 Lipton .................... G06T 5/001
382/154

(Continued)

FOREIGN PATENT DOCUMENTS

EP 2 339 858 A2 6/2011
JP 8-76027 A 3/1996
(Continued)

OTHER PUBLICATIONS

Extended European Search Report dated Feb. 10, 2020, issued in corresponding European Patent Application No. 17899671.6.

(Continued)

*Primary Examiner* — Irfan Habib
(74) *Attorney, Agent, or Firm* — Xsensus LLP

(57) ABSTRACT

[Problem] Both the synchronization between multiple devices for the timing in which a left-eye image and a right-eye image forming a medical image are displayed and the suppression of the delay in presenting an image to a predetermined viewer are enabled.
[Solution] A medical-image display control device includes: a display controller that controls a medical image so as to be displayed on a slave-side display unit; and an acquiring unit that acquires, from another device including a master-side display unit different from the slave-side display unit, a synchronization signal that corresponds to timing in which (Continued)

the other device displays a left-eye image and a right-eye image on the master-side display unit, and the display controller controls a left-eye image and a right-eye image so as to be displayed on the slave-side display unit in a time-division manner in accordance with the acquired synchronization signal.

20 Claims, 12 Drawing Sheets

(56) References Cited

U.S. PATENT DOCUMENTS

| | | | | |
|---|---|---|---|---|
| 9,077,984 B2* | 7/2015 | Yoshida | | H04N 13/334 |
| 9,247,240 B2* | 1/2016 | Park | | H04N 13/341 |
| 9,294,761 B2* | 3/2016 | Lee | | H04N 13/341 |
| 9,910,257 B2* | 3/2018 | Ward | | G02B 21/361 |
| 2010/0067768 A1* | 3/2010 | Ionasec | | G06T 7/35 |
| | | | | 382/131 |
| 2011/0135173 A1* | 6/2011 | Elbaroudi | | G06T 7/0012 |
| | | | | 382/128 |
| 2011/0157318 A1* | 6/2011 | Nalibotski | | H04N 13/161 |
| | | | | 348/47 |
| 2011/0234586 A1* | 9/2011 | Aoki | | H04N 13/341 |
| | | | | 345/419 |
| 2012/0169852 A1* | 7/2012 | Seo | | H04N 13/341 |
| | | | | 348/56 |
| 2012/0230568 A1* | 9/2012 | Grbic | | G06K 9/6289 |
| | | | | 382/131 |
| 2012/0281900 A1* | 11/2012 | Rueckert | | G06T 7/149 |
| | | | | 382/131 |
| 2013/0129174 A1* | 5/2013 | Grbic | | G06T 7/0012 |
| | | | | 382/131 |
| 2013/0194399 A1* | 8/2013 | Wirtz | | H04N 13/398 |
| | | | | 348/53 |
| 2013/0257860 A1* | 10/2013 | Tezuka | | G06T 15/00 |
| | | | | 345/419 |
| 2014/0078271 A1* | 3/2014 | Oda | | H04N 13/398 |
| | | | | 348/56 |

FOREIGN PATENT DOCUMENTS

| | | |
|---|---|---|
| JP | 2000-236455 A | 8/2000 |
| JP | 2011-188232 A | 9/2011 |
| JP | 2012-227678 A | 11/2012 |
| JP | 2014-116942 A | 6/2014 |
| WO | 2012/010500 A2 | 1/2012 |

OTHER PUBLICATIONS

International Search Report and Written Opinion dated Jan. 23, 2018 for PCT/JP2017/038920 filed on Oct. 27, 2017, 10 pages including English Translation of the International Search Report.

* cited by examiner

MEDICAL-IMAGE DISPLAY CONTROL DEVICE, MEDICAL IMAGE DISPLAY DEVICE, MEDICAL-INFORMATION PROCESSING SYSTEM, AND MEDICAL-IMAGE DISPLAY CONTROL METHOD

CROSS-REFERENCE TO RELATED APPLICATIONS

The present application is based on PCT filing PCT/JP2017/038920, filed Oct. 27, 2017, which claims priority to JP 2017-046099, filed Mar. 10, 2017, the entire contents of each are incorporated herein by reference.

TECHNICAL FIELD

The present disclosure relates to a medical-image display control device, a medical-image display device, a medical-information processing system, and a medical-image display control method.

BACKGROUND ART

In recent years, surgeries (what is called, microsurgeries) for giving various types of treatment while observing the diseased site with a medical observation apparatus, such as surgical microscope or endoscope, have been frequently performed due to improvements in surgical techniques and surgical instruments. Furthermore, this kind of medical observation apparatus includes not only an apparatus that enables optical observation on the diseased site but also an apparatus that causes a display device, e.g., a display, to present an image of the diseased site captured by an imaging unit (camera), or the like, as an electronic image.

Furthermore, when an image (hereafter, referred to as "medical image") of the diseased site captured by an imaging unit of the observation apparatus is displayed on a display device, the image is often displayed as a planar two-dimensional (2D) image. With 2D images, however, it is difficult to have a sense of perspective and is difficult to determine a relative distance between a diseased site and a treatment tool; therefore, technologies have been recently developed to display the captured image of the diseased site as a solid three-dimensional (3D) image.

With the observation apparatus (hereafter, referred to as "stereoscopic observation apparatus" in some cases) that displays the captured image of the diseased site as a solid three-dimensional (3D) image as described above, for example, different viewpoint images are observed by the right and left eyes so that the user observes the image of the diseased site as a solid three-dimensional image. Moreover, in the present disclosure, for convenience, the viewpoint image observed by the left eye is also referred to as "left-eye image", and the viewpoint image observed by the right eye is also referred to as "right-eye image".

Particularly, a shutter-glasses method has been recently popular as a method for achieving observation of three-dimensional images in accordance with an increase in the resolution (higher definition) of display devices. The shutter-glasses method is a method for achieving observation of three-dimensional images by displaying a left-eye image and a right-eye image on the display device in a time-division manner and causing the shutter glasses to individually observe the left-eye image and the right-eye image.

CITATION LIST

Patent Literature

Patent Literature 1: Japanese Laid-open Patent Publication No. 2014-116942

DISCLOSURE OF INVENTION

Technical Problem

Furthermore, in medical practice where the above-described medical observation apparatus is used, there may be assumed circumstances where various types of information are presented by using a plurality of displays (i.e., display devices) and the information (image) presented on each display device is viewed by multiple viewers including the operator. To be able to observe three-dimensional images based on the shutter-glasses method in such a situation, there is a need to generate the synchronization between multiple display devices or the synchronization between the display device and the shutter glasses worn by each viewer. For example, Patent Literature 1 discloses an example of the technology for generating the synchronization between multiple display devices and multiple pairs of shutter glasses.

As a method for generating the above-described synchronization in real time, for example, there is a known method for generating the synchronization by delaying the timing in which an image is displayed on each display device. In a situation where the operator conducts various types of surgeries while checking an image of the surgical site, however, it is sometimes more important to minimize the delay when the image of the surgical site (diseased site) is presented to a predetermined viewer such as the operator.

Therefore, the present disclosure discloses the technology that enables both the synchronization between multiple devices for the timing in which the left-eye image and the right-eye image forming the medical image are displayed and the suppression of the delay in presenting an image to a predetermined viewer.

Solution to Problem

According to the present disclosure, there is provided a medical-image display control device including: a display controller that controls a medical image so as to be displayed on a slave-side display unit; and an acquiring unit that acquires, from another device including a master-side display unit different from the slave-side display unit, a synchronization signal that corresponds to timing in which the other device displays a left-eye image and a right-eye image forming a medical image on the master-side display unit, wherein the display controller controls a left-eye image and a right-eye image forming a medical image so as to be displayed on the slave-side display unit in a time-division manner in accordance with the synchronization signal acquired.

Moreover, according to the present disclosure, there is provided a medical-image display device including: a display unit; a display controller that controls a left-eye image and a right-eye image forming a medical image so as to be displayed on the display unit in a time-division manner; and a transmitting unit that transmits a synchronization signal that corresponds to timing in which a left-eye image and a right-eye image forming a medical image are displayed on the display unit.

Moreover, according to the present disclosure, there is provided a medical-information processing system including a plurality of devices, wherein any device among the devices operates as a master device, and another device that is different from the master device operates as a slave device, the master device controls a left-eye image and a right-eye image forming a medical image so as to be displayed on a master-side display unit in a time-division manner, and transmits a synchronization signal that corresponds to timing in which the left-eye image and the right-eye image are displayed, and the slave device acquires the synchronization signal and controls a left-eye image and a right-eye image forming a medical image so as to be displayed in a time-division manner on a slave-side display unit different from the master-side display unit in accordance with the synchronization signal.

Moreover, according to the present disclosure, there is provided a medical-image display control method causing a computer to execute: controlling a medical image so as to be displayed on a slave-side display unit; acquiring, from another device including a master-side display unit different from the slave-side display unit, a synchronization signal that corresponds to timing in which the other device displays a left-eye image and a right-eye image forming a medical image on the master-side display unit; and displaying a left-eye image and a right-eye image forming a medical image so as to be displayed on the slave-side display unit in a time-division manner in accordance with the synchronization signal acquired.

Moreover, according to the present disclosure, there is provided a medical-image display control method causing a computer to execute: controlling a left-eye image and a right-eye image forming a medical image so as to be displayed on a predetermined display unit in a time-division manner; and transmitting a synchronization signal that corresponds to timing in which a left-eye image and a right-eye image forming a medical image are displayed on the display unit.

Advantageous Effects of Invention

As described above, the present disclosure provides the technology that enables both the synchronization between multiple devices for the timing in which the left-eye image and the right-eye image are displayed and the suppression of the delay in presenting an image to a predetermined viewer.

Furthermore, the above-described advantageous effect is not always a limitation, but any advantageous effect described in this description or other advantageous effects that may be determined from this description may be produced together with the above-described advantageous effect or instead of the above-described advantageous effect.

BEST MODE FOR CARRYING OUT THE INVENTION

Figure 1:
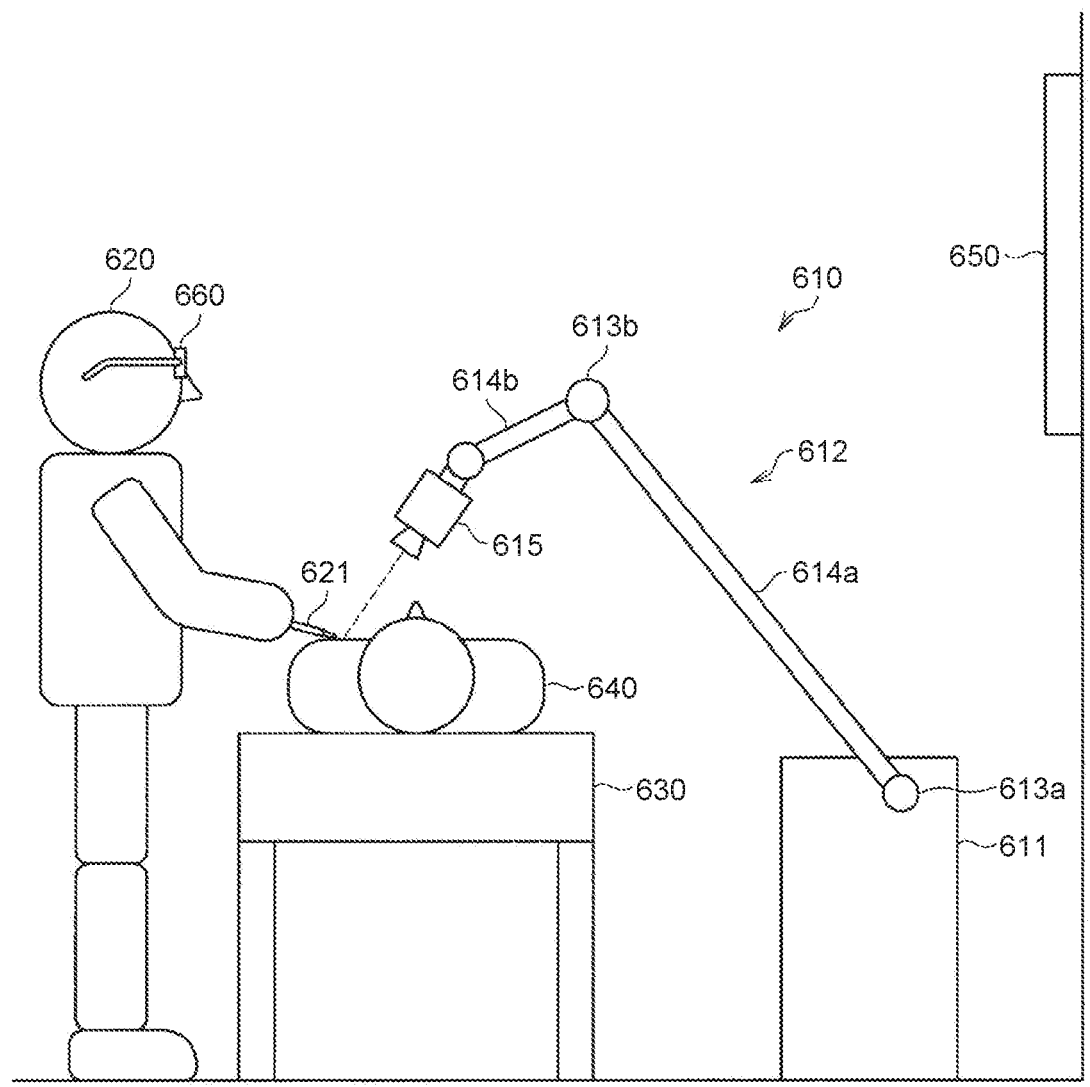
FIG. 1 is an explanatory diagram that illustrates an example of the schematic configuration of a medical stereoscopic observation apparatus according to an embodiment of the present disclosure.

With reference to the accompanying drawings, a preferred embodiment according to the present disclosure is explained below in detail. Furthermore, in the description and the drawings, components having substantially the same functional configuration are attached with the same reference numeral and therefore duplicated explanations are omitted.

Further, explanations are given in the following order.
1. Schematic configuration of a medical stereoscopic observation apparatus
2. Consideration on presentation of three-dimensional image
3. Technical feature
   3.1. Schematic configuration
   3.2. Functional configuration
   3.3. Process
   3.4. Modification
4. Application example
   4.1. First application example: rigid endoscope device
   4.2. Second application example: flexible endoscope device
5. Hardware configuration
6. Conclusion
   <<1. Schematic Configuration of the Medical Stereoscopic Observation Apparatus>>

First, to further clarify the present disclosure, an explanation is given of an example of the schematic configuration of the medical stereoscopic observation apparatus according to an embodiment of the present disclosure.

For example, FIG. 1 is an explanatory diagram that illustrates an example of the schematic configuration of the medical stereoscopic observation apparatus according to the embodiment of the present disclosure. FIG. 1 illustrates an example of the case where a surgical video microscope apparatus having an arm is used as the medical stereoscopic observation apparatus according to an application example where the medical stereoscopic observation apparatus according to the embodiment of the present disclosure is used.

For example, FIG. 1 schematically illustrates the situation of operation using the surgical video microscope apparatus according to the present embodiment. Specifically, in the situation described with reference to FIG. 1, a doctor, who is a practitioner (user) 620, performs a surgical procedure on a subject (patient) 640 on an operation bed 630 by using a surgical tool 621 such as scalpel, tweezers, or forceps. Further, in the following explanation, the operation is the generic term for various types of medical treatments, such as surgical procedures or examinations, conducted on the patient, the subject 640, by the doctor, the user 620. Moreover, FIG. 1 illustrates an example of the situation of the surgical procedure as an example of the operation; however, the operation using a surgical video microscope apparatus 610 is not limited to surgical procedures, and it may be other various types of operations, e.g., examinations using an endoscope.

The surgical video microscope apparatus 610 according to the present embodiment is disposed on the side of the operation bed 630. The surgical video microscope apparatus 610 includes: a base unit 611 that is the base; an arm unit 612 that extends from the base unit 611; and a capturing unit 615 that is a distal end unit connected to the distal end of the arm unit 612. The arm unit 612 includes a plurality of joint units 613a, 613b, 613c, a plurality of links 614a, 614b connected with the joint units 613a, 613b, and the capturing unit 615 disposed at the distal end of the arm unit 612. In the example illustrated in FIG. 1, for simplification, the arm unit 612 includes the three joint units 613a to 613c and the two links 614a, 614b; however, in actuality, in consideration of the flexibility in the positions and the postures of the arm unit 612 and the capturing unit 615, it is possible to optionally set the number and the shape of the joint units 613a to 613c and the links 614a, 614b, the direction of the drive shaft of the joint units 613a to 613c, and the like, so as to achieve the desired flexibility.

The joint units 613a to 613c have a function to connect the links 614a, 611b in a rotatable manner relative to each other, and driving of the arm unit 612 is controlled by driving the rotation of the joint units 613a to 613c. Here, in the following explanation, the position of each component of the surgical video microscope apparatus 610 refers to the position (coordinates) in the space defined for driving control, and the posture of each component refers to the direction (angle) relative to any given axis in the space defined for driving control. Further, in the following explanation, driving (or driving control) of the arm unit 612 refers to driving (or driving control) of the joint units 613a to 613c and changes (control on changes) in the position and the posture of each component of the arm unit 612 by conducting driving (or driving control) of the joint units 613a to 613c.

The capturing unit 615, which is a distal end unit, is coupled to the distal end of the arm unit 612. The capturing unit 615 is a unit that acquires the target image (i.e., medical image) to be captured, and it is for example a camera capable of capturing moving images and still images. As illustrated in FIG. 1, the postures and the positions of the arm unit 612 and the capturing unit 615 are controlled by the surgical video microscope apparatus 610 so that the capturing unit 615 provided at the distal end of the arm unit 612 captures the state of the treatment site of the subject 640. Furthermore, there is no particular limitation on the configuration of the capturing unit 615 that is the distal end unit coupled to the distal end of the arm unit 612, and the capturing unit 615 may be configured as, for example, an endoscope or a microscope. Furthermore, the capturing unit 615 may be configured such that it is attachable to and detachable from the arm unit 612. With this configuration, for example, the capturing unit 615 may be optionally coupled to the distal end of the arm unit 612 as a distal end unit depending on a use application. Moreover, although an explanation is primarily given of a case where the capturing unit 615 is applied as a distal end unit in this description, it is obvious that the distal end unit coupled to the distal end of the arm unit 612 is not always limited to the capturing unit 615.

Furthermore, a display device 650, such as a monitor or a display, is placed at the position opposed to the user 620. An image of the treatment site captured by the capturing unit 615 is displayed as an electronic image on the display screen of the display device 650. The user 620 conducts various types of treatment while viewing the electronic image of the treatment site displayed on the display screen of the display device 650.

Thus, the present embodiment discloses, in a medical field, a surgery performed while capturing a treatment site with the surgical video microscope apparatus 610.

Particularly, the surgical video microscope apparatus 610 (i.e., the medical stereoscopic observation apparatus) according to the embodiment of the present disclosure is configured such that it is capable of acquiring image data for displaying the target to be captured as a three-dimensional image (3D image).

According to a specific example, the surgical video microscope apparatus 610 is provided with, as the capturing unit 615, a stereo camera including imaging units (e.g., camera units) in two systems so as to acquire images (i.e., viewpoint images) from different viewpoints via the respective imaging units.

Each of the viewpoint images (i.e., viewpoint images forming a medical image) acquired by the capturing unit 615 is subjected to various types of image processing by, for example, an image processing device built in or eternally connected to the surgical video microscope apparatus 610 and is displayed on the display device 650 as the left-eye image and the right-eye image (i.e., the left-eye image and the right-eye image forming the medical image). Here, in this description, the right-eye image represents what is called a disparity image for which the disparity is set for observation at the viewpoint corresponding to the user's right eye so that the user observes a 3D image. Similarly, the left-eye image represents a disparity image for which the disparity is set for observation at the viewpoint corresponding to the user's left eye so that the user observes a 3D image.

Furthermore, various methods have been disclosed as a system for causing the user 620 to observe, as a three-dimensional image, the image displayed as a left-eye image and a right-eye image on the display device 650. In a specific example, there is a shutter-glasses method in which, by using dedicated glasses called shutter glasses, other images (i.e., a left-eye image and a right-eye image) are observed by the right and left eyes in a time-division manner. For example, in the example illustrated in FIG. 1, the user 620 views the electronic image of the treatment site displayed on the display device 650 through shutter glasses 660, thereby observing a three-dimensional image of the treatment site.

Furthermore, in the circumstance where the above-described medical observation apparatus is used, various types of information including an image of the diseased site sometimes needs to be checked, and under such a circumstance, there is an assumed type of usage, for example, an image is displayed on each of the display units, or multiple images are displayed on the display unit. In a specific example, there is an assumed case in which the full image of the diseased site is displayed on one of the display units, and the enlarged image of the diseased site is displayed on the other one of the display units. Moreover, in another example, there is an assumed case in which the image of the diseased site is displayed on one of the display units and the image captured by another imaging device, such as CT (Computed Tomography) image or an MRI (Magnetic Resonance Imaging) image, is displayed on the other one of the display units. For this reason, there is a case where the multiple display devices 650 are provided.

As an example of the application where the medical stereoscopic observation apparatus according to the embodiment of the present disclosure is used, the explanation is given above, with reference to FIG. 1, of an example of the case where the surgical video microscope apparatus including the arm is used as the medical stereoscopic observation apparatus.

<<2. Consideration on Presentation of Three-Dimensional Image>>

Next, an effect on various methods for conducting observation on a three-dimensional image in association with a high definition of the display is explained, and then a problem of the medical-information processing system and the medical stereoscopic observation apparatus according to the embodiment of the present disclosure is summarized.

First, the summary of an example of the method for conducting observation on a three-dimensional image is explained. The method for conducting observation on a three-dimensional image includes, for example, a passive method and an active shutter method. The passive method and the active shutter method are a method for causing a user to observe a solid three-dimensional image by causing the right and the left eyes to observe the corresponding images (i.e., a left-eye image and a right-eye image), while the passive method and the active shutter method are different in the mechanism for observing a three-dimensional image, i.e., the mechanism for causing the right and the left eyes to observe the corresponding images. Specifically, the passive method is a method in which both a right-eye image and a left-eye image are displayed on the screen of the display device and the right-eye image and the left-eye image are separated by a polarization filter, a color filter, or the like, so that each of the right and the left eyes is caused to observe the corresponding image. Furthermore, the shutter-glasses method is a method in which a left-eye image and a right-eye image are displayed in a time-division manner on the screen of the display device and the left-eye shutter and the right-eye shutter provided in the shutter glasses are opened and closed in synchronization with the timing in which the respective images are displayed so that each of the right and the left eyes is caused to observe the corresponding image.

Figure 2:
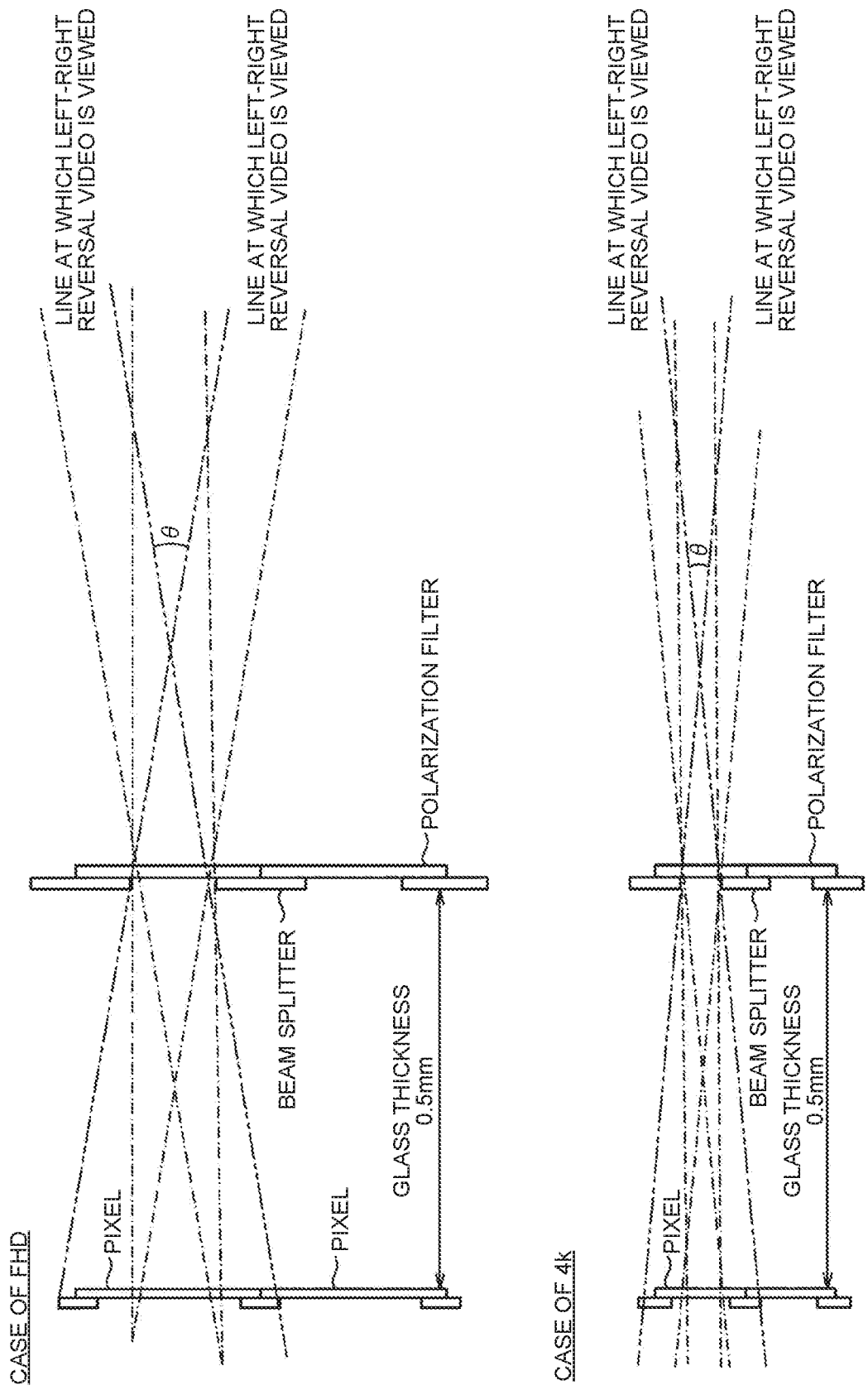
FIG. 2 is an explanatory diagram that illustrates an effect associated with an increase in the resolution of a display when the passive method is applied.

Conventionally, in medical practice where the above-described medical stereoscopic observation apparatus is used, the passive method is primarily used as the method for conducting observation on three-dimensional images. However, in recent years, it has been difficult to use the passive method due to an increase in the resolution of a display device such as a display. For example, FIG. 2 is an explanatory diagram that illustrates an effect associated with an increase in the resolution of a display when the passive method is applied, and it illustrates an example of the schematic configuration for observing a three-dimensional image based on the passive method. Specifically, FIG. 2 illustrates an example of the schematic configuration of the display panel of a display device when the display panel is cut on the plane perpendicular to both the horizontal plane and the display surface of the display panel and the cut surface is viewed from the side surface side of the display device. Furthermore, the up-and-down direction in FIG. 2 is equivalent to the up-and-down direction (vertical direction) of the display panel of the display device, and the depth direction in FIG. 2 is equivalent to the right-and-left direction (horizontal direction) of the display panel. That is, the right-and-left direction in FIG. 2 is equivalent to the front-back direction when the display panel is opposed. Furthermore, in FIG. 2, the upper diagram illustrates an example when the resolution is FHD (1920×1080 pixels). Moreover, the lower diagram illustrates an example when the resolution is 4K (3840×2160).

When the passive method is adopted, an optical member having polarization properties, such as a pattern retarder, is provided in front of the display panel to separate a left-eye image and a right-eye image displayed on the display panel. For example, in FIG. 2, a beam splitter and a polarization filter are equivalent to the optical member such as the above-described pattern retarder. Specifically, as illustrated in FIG. 2, light from each pixel passes through the beam splitter located in front of the pixel and is then polarized by the polarization filter. In this manner, light from each pixel is individually separated. Thus, light from a pixel used for displaying a left-eye image and light from a pixel used for displaying a right-eye image are separated so that each of them may be observed by the corresponding eye (that is, a three-dimensional image may be observed).

However, when the passive method is adopted, a phenomenon called crosstalk sometimes occurs, that is, an image different from the corresponding image is observed by each of the right and the left eyes (i.e., the right-eye image is observed by the left eye, and the left-eye image is observed by the right eye) depending on the position (hereafter, also referred to as "viewing position") of the viewer relative to the display device.

Specifically, as illustrated in FIG. 2, in addition to light from the pixel, light from another pixel adjacent to the pixel sometimes escapes from the beam splitter located in front of the pixel. Therefore, for example, outside the vertical viewing angle indicated by the reference numeral θ in FIG. 2, the right and the left eyes observe the video that is reverse to the video that is supposed to be observed, which sometimes results in observation of a video with fuzzy outline or video with degraded appearance of solidity.

With such a configuration, as it is understood from the comparison between the cases of FHD and 4 k illustrated in FIG. 2, the vertical viewing angle θ is narrower as the pixel pitch is narrower if the pixel pitch is changed without changing the glass thickness of the display panel. Therefore, if the high resolution (high definition) of the display panel further improved in the future, it may be assumed that it is practically difficult to ensure the vertical viewing angle θ without adjusting the glass thickness so as to further reduce the thickness. Furthermore, in accordance with an increase in the resolution of the display panel, a stricter condition for the accuracy is needed when an optical member such as a pattern retarder is attached to the display panel. Moreover, when the passive method is adopted, there is a need to attach an optical member such as a pattern retarder to the display panel and therefore a dedicated display device needs to be used.

However, with the shutter-glasses method, as described above, a left-eye image and a right-eye image are displayed in a time-division manner so that observation of a three-dimensional image is conducted. Due to this feature, the shutter-glasses method enables display of a left-eye image and a right-eye image (eventually, observation of a three-dimensional image) by controlling software without using a dedicated display device as in the passive method. Furthermore, the above-described feature prevents the occurrence of crosstalk that is caused by the structure of the display panel and an optical member attached to the display panel as in the passive method, and therefore there is no need to consider the restriction of the above-described viewing angle θ as in the passive method. Because of this feature, the shutter-glasses method has been popular as the method for conducting observation of a three-dimensional image in accordance with an increase in the resolution of the display device.

Furthermore, with the shutter-glasses method, there is a need to control a left-eye shutter and a right-eye shutter so as to be opened and closed in synchronization with the timing in which a left-eye image and a right-eye image are displayed on the display device.

Specifically, in the medical practice where the medical stereoscopic observation apparatus is used as described above with reference to FIG. 1, various medical images (e.g., an image of the diseased site, an image of the surgical field, or other modal images) are sometimes presented by using a plurality of display devices. Specifically, in an assumed situation, a certain viewer (e.g., an operator) views an image displayed in each of the display devices and, in such a case, there is a need to take account of synchronization of the timing in which the left-eye image and the right-eye image are displayed on the display devices.

Furthermore, in the medical practice, the viewer who views various medical images displayed in each display device is not always the single operator who conducts a surgery, but there is an assumed situation where multiple viewers including, for example, assistant, anesthetist, or nurse, views a medical image displayed on each display device. That is, there is an assumed situation where a medical image displayed on a certain display device is viewed by multiple viewers and, in this case, there is a need to consider the synchronization of the timing in which the left-eye image and the right-eye image are displayed on the display device and the timing in which the shutters of the shutter glasses worn by each viewer are opened and closed. Of course, it is also possible to assume a situation where each of the viewers views a medical image displayed in each of the display devices.

Here, for example, there is a known method in which the timing in which an image is displayed in each display device is delayed for the synchronization if it is assumed that the display of an image in each of the display devices is synchronized among the display devices in real time. However, in a situation where an operator performs various surgeries while checking the image of the surgical site by using the above-described medical stereoscopic observation apparatus, it is sometimes more important to suppress the delay to a minimum when an image (i.e., medical image) of the surgical site (the diseased site) is presented to a predetermined viewer such as the operator.

In consideration of such a circumstance, the present disclosure discloses an example of the technology that achieves both the synchronization between multiple display devices for the timing in which the left-eye image and the right-eye image are displayed and the suppression of the delay in presenting an image (i.e., medical image) to a predetermined viewer such as operator. Hereafter, the medical-information processing system according to the embodiment of the present disclosure is explained in more detail with a focus on a technical feature.

<<3. Technical Feature>>

Next, as the medical-information processing system according to the embodiment of the present disclosure, an example of the system that presents an image of the diseased site to a viewer such as operator by the use of the above-described medical stereoscopic observation apparatus is explained with a focus on, particularly, the technical feature of the system.

<3.1. Schematic Configuration>

Figure 3:
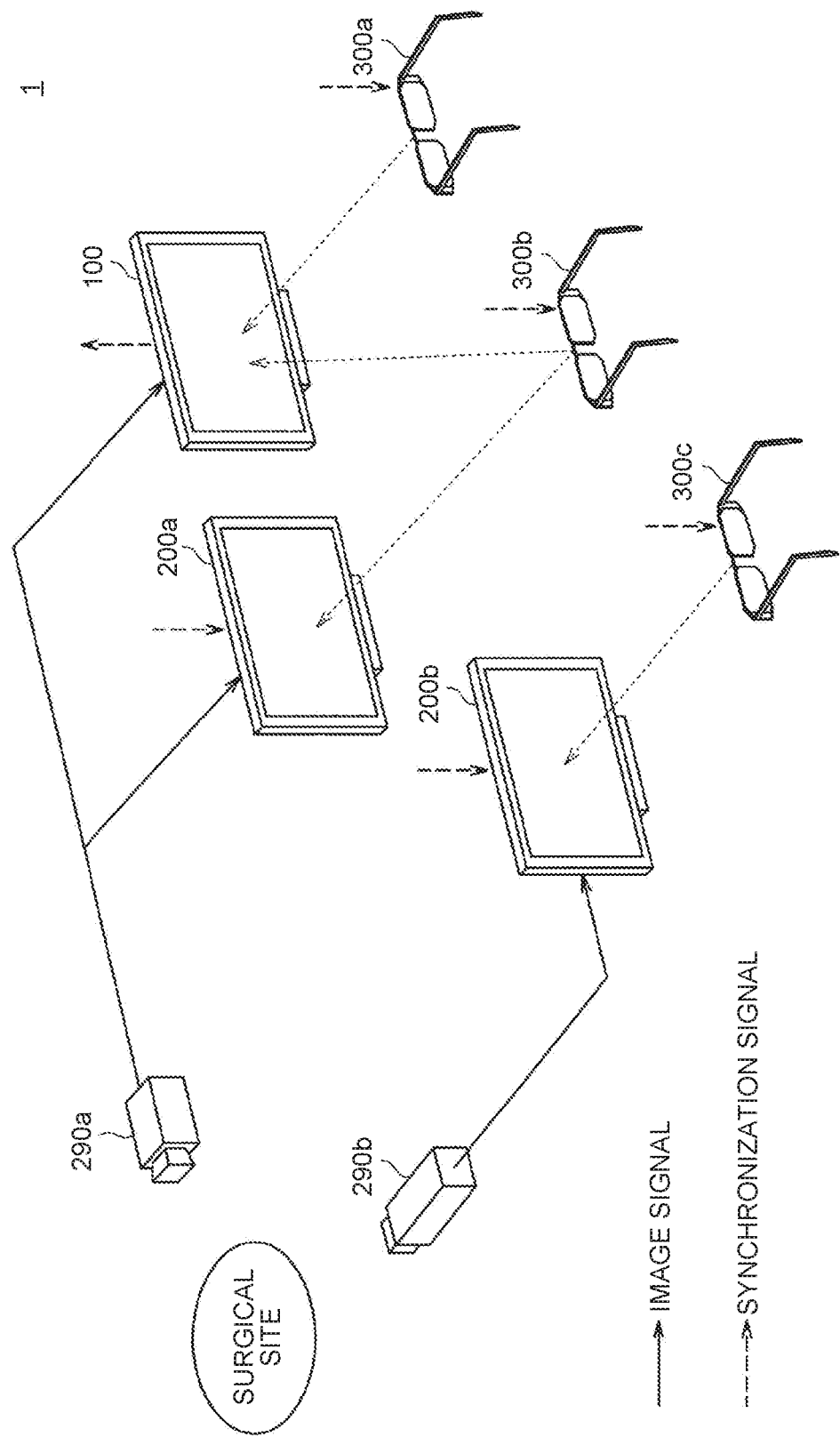
FIG. 3 is an explanatory diagram that illustrates an example of the schematic system configuration of a medical-information processing system according to the present embodiment.

First, with reference to FIG. 3, an explanation is given of an example of the schematic system configuration of the medical-information processing system according to the present embodiment. FIG. 3 is an explanatory diagram that illustrates an example of the schematic system configuration of the medical-information processing system according to the present embodiment.

FIG. 3 illustrates an example of the system configuration when it is assumed that an operator performs various surgeries while checking the video of the surgical site (the diseased site) of a patient by the use of an imaging device 290 (i.e., medical imaging device or medical capturing unit) such as surgical microscope, endoscope, surgical-field camera, or surgical camera. For example, the reference marks 290a and 290b denote examples of the above-described imaging device 290. In other words, the medical stereoscopic observation apparatus described with reference to FIG. 1 is applicable as at least any one of the imaging devices 290a and 290b.

Furthermore, in FIG. 3, the reference numeral 100 denotes the main display device used to check the video of the surgical site so that the operator conducts a surgery. Furthermore, the reference marks 200a and 200b denote display devices different from the display device 100. The display devices 200a and 200b may be used to display medical images (e.g., other modal images such as CT (Computed Tomography) or MRI (Magnetic Resonance Imaging)) different from the medical image displayed on the display device 100. Furthermore, according to another example, the display devices 200a and 200b may be used to display the video of the surgical site so that other viewers (e.g., assistant, anesthetist, or nurse) other than the operator checks the surgical site. Furthermore, in the following explanation, the display device 100 is also referred to as "the master display device 100", and each of the display devices 200a and 200b is also referred to as "slave display device 200".

Furthermore, a medical-information processing system 1 according to the present embodiment causes each viewer such as operator, assistant, anesthetist, or nurse, to observe the target medical image (e.g., the image of the surgical site captured by the imaging unit 290) to be displayed as a three-dimensional image on the basis of the shutter-glasses method. In FIG. 3, the reference marks 300a to 300c denote shutter glasses for observing three-dimensional images based on the shutter-glasses method. Furthermore, in the following explanation, the shutter glasses 300a to 300b are also simply referred to as "shutter glasses 300" when they are not particularly distinguished. Moreover, for convenience in this description, the shutter glasses 300a represent the shutter glasses 300 worn by the operator who conducts various surgeries, and the other shutter glasses 300b and 300c represent the shutter glasses 300 worn by viewers, such as assistant, anesthetist, or nurse, other than the operator.

Based on the above configuration, the medical-information processing system 1 according to the present embodiment minimizes a delay in displaying an image (i.e., a left-eye image and a right-eye image) on the master display device 100 that is included in multiple display devices and is used to check the surgical site when the operator, the main viewer, conducts a surgery. Based on this assumption, the medical-information processing system 1 enables first synchronization among the display devices 100, 200a, and 200b and second synchronization between the display devices 100, 200a, and 200b and the shutter glasses 300a to 300b. Here, the first synchronization represents the synchronization of the timing in which a left-eye image and a right-eye image are displayed on the display devices 100, 200a, and 200b. Furthermore, the second synchronization represents the synchronization between the timing in which a left-eye image and a right-eye image are displayed in the display devices 100, 200a, and 200b and the shutter control on each pair of the shutter glasses 300a to 300b.

As a specific example, in the example of the case illustrated in FIG. 3, the master display device 100 causes the display unit (e.g., the display panel) to display the left-eye image and the right-eye image that correspond to the imaging result by the imaging device 290a in a time-division manner in accordance with the synchronization signal generated by itself. Due to this control, it is possible to minimize the delay before the image (i.e., medical image) of the surgical site captured by the imaging device 290a is displayed on the display unit of the master display device 100.

Furthermore, the master display device 100 transmits the synchronization signal (i.e., the synchronization signal generated by itself) that corresponds to the timing in which the left-eye image and the right-eye image are displayed to each of the slave display devices 200a and 200b and each pair of the shutter glasses 300a to 300c. Furthermore, there is no limitation on the method for transmitting the synchronization signal. As a specific example, the master display device 100 may transmit a synchronization signal to each of the slave display devices 200a and 200 and each pair of the shutter glasses 300a to 300c on the basis of a communication via a predetermined network. Here, the master display device 100 may transmit the synchronization signal by explicitly designating the transmission destination or may distribute the synchronization signal to the peripheral devices without explicitly designating the transmission destination during what is called broadcast or multicast. Furthermore, as another example, the master display device 100 may transmit the synchronization signal by the use of infrared signals, or the like. In this case, each of the slave display devices 200a and 200 and each pair of the shutter glasses 300a to 300c may be provided with a light receiving unit that receives the infrared signals, or the like.

Each of the slave display devices 200a and 200b delays the timing in which a left-eye image and a right-eye image are displayed in accordance with the synchronization signal transmitted from the master display device 100, thereby causing the display unit to display the left-eye image and the right-eye image in synchronization with the synchronization signal. This control allows the synchronization between the timing in which each of the left-eye image and the right-eye image is displayed on the master display device 100 and the timing in which each of the left-eye image and the right-eye image is displayed in each of the slave display devices 200a and 200b.

Each of the shutter glasses 300a to 300c controls the left-eye shutter and the right-eye shutter so as to be opened and closed in accordance with the synchronization signal transmitted from the master display device 100. This control allows the synchronization between the timing in which the left-eye image and the right-eye image are displayed in the master display device 100 and the timing in which the left-eye shutter and the right-eye shutter are opened and closed in each pair of the shutter glasses 300a to 300c. Furthermore, as described above, the timing in which a left-eye image and a right-eye image are displayed are synchronized between the master display device 100 and each of the slave display devices 200a and 200b. Therefore, the timing in which each of the left-eye image and the right-eye image is displayed in each of the slave display devices 200a and 200b is synchronized with the timing in which the left-eye shutter and the right-eye shutter are opened and closed in each of the shutter glasses 300a to 300c.

The above configuration allows a certain viewer to view a three-dimensional image without fail even in a situation where the viewer views each image displayed in the master display device 100 and each of the slave display devices 200 via the shutter glasses 300 worn by him/herself. Furthermore, each viewer is capable of viewing a three-dimensional image without fail even in a situation where multiple viewers view images displayed in the master display device 100 and each of the slave display devices 200 via the shutter glasses 300 worn by themselves.

Furthermore, the configuration of the above-described medical-information processing system 1 is merely an example, and the configuration of the medical-information processing system 1 is not limited to the example illustrated in FIG. 3 as long as the slave display devices 200 and the shutter glasses 300 are operated in synchronization with one another based on the synchronization signal from the master display device 100. For example, the medical images displayed in the master display device 100 and the slave display devices 200 are not limited to only images captured by the various imaging devices 290. For example, medical images previously acquired by other modals such as CT or MRI and stored in a predetermined storage device may be displayed in the master display device 100 or each of the slave display devices 200. In such a case, the information writing system 1 does not need to include the imaging device 290.

An example of the schematic system configuration of the medical-information processing system according to the present embodiment has been explained above with reference to FIG. 3.

<3.2. Functional Configuration>

Figure 4:
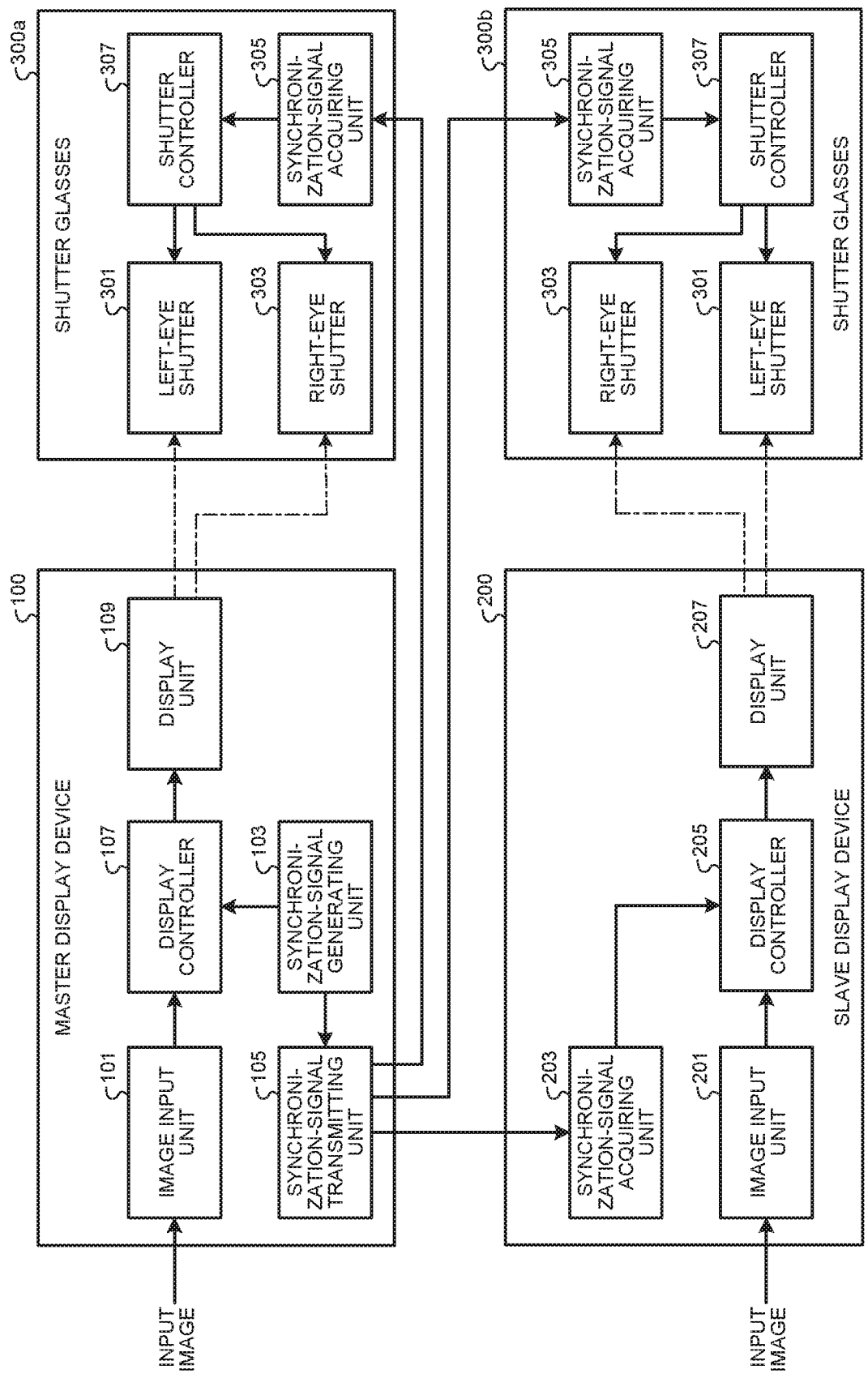
FIG. 4 is a block diagram that illustrates an example of the functional configuration of the medical-information processing system according to the present embodiment.

Next, with reference to FIG. 4, an example of the functional configuration of the medical-information processing system 1 according to the present embodiment is explained. FIG. 4 is a block diagram that illustrates an example of the functional configuration of the medical-information processing system 1 according to the present embodiment. Furthermore, among the configurations of the medical-information processing system 1 described with reference to FIG. 3, particularly, the configurations of the master display device 100, the slave display device 200, and the shutter glasses 300 are explained in this description. Here, the example illustrated in FIG. 3 illustrates the shutter glasses 300a and 300b as the shutter glasses 300.

(The Master Display Device 100)

First, the configuration of the master display device 100 is explained. As illustrated in FIG. 4, the master display device 100 includes an image input unit 101, a synchronization-signal generating unit 103, a synchronization-signal transmitting unit 105, a display controller 107, and a display unit 109.

The display unit 109 corresponds to the display panel of the master display device 100. The display unit 109 displays the target image to be displayed based on the control by the display controller 107 described later. Furthermore, the display unit 109 corresponds to an example of a "master-side display unit".

The image input unit 101 corresponds to an input interface for inputting image data on the target image to be displayed. For example, image data based on the imaging result by each of the imaging devices 290 illustrated in FIG. 3 is input to the master display device 100 via the image input unit 101. Further, image data input via the image input unit 101 is also referred to as "input image data" below.

The synchronization-signal generating unit 103 generates a synchronization signal for displaying a left-eye image and a right-eye image, which correspond to input image data, in a time-division manner (i.e., a synchronization signal that corresponds to the timing in which each of the left-eye image and the right-eye image is displayed). The synchronization-signal generating unit 103 feeds the generated synchronization signal to each of the display controller 107 and the synchronization-signal transmitting unit 105.

The synchronization-signal transmitting unit 105 transmits a synchronization signal fed from the synchronization-signal generating unit 103 to the slave display device 200 and the shutter glasses 300. Furthermore, as described above, there is no particular limitation on the method for transmitting synchronization signals. Therefore, the configuration of the synchronization-signal transmitting unit 105 may be changed as needed depending on the method for transmitting synchronization signals. For example, the synchronization-signal transmitting unit 105 may include a baseband processor, RF (Radio Frequency) circuitry, or the like, when synchronization signals are transmitted via a wireless communication path.

The display controller 107 causes the display unit 109 to display the left-eye image and the right-eye image, which correspond to the input image data input via the image input unit 101, in a time-division manner in accordance with a synchronization signal fed from the synchronization-signal generating unit 103. Furthermore, the display controller 107 corresponds to an example of a "master-side display controller".

Furthermore, there is no particular limitation on the generation source of a left-eye image and a right-eye image. In a specific example, a left-eye image and a right-eye image may be images captured from multiple viewpoints by the imaging device 290 including a plurality of imaging units, such as what is called a stereo camera, and image data on the left-eye image and the right-eye image may be output from the imaging device 290. Furthermore, in another example, the display controller 107 may generate a left-eye image and a right-eye image based on image data that corresponds to an imaging result by the imaging device 290, such as what is called a monocular camera. Moreover, the display controller 107 may here generate a left-eye image and a right-eye image based on image data that corresponds to the image by using a measurement result of the distance to the object captured in the image by a distance measurement sensor, or the like.

(The Slave Display Device 200)

Next, the configuration of the slave display device 200 is explained. As illustrated in FIG. 4, the slave display device 200 includes an image input unit 201, a synchronization-signal acquiring unit 203, a display controller 205, and a display unit 207. Furthermore, as the image input unit 201 and the display unit 207 have substantially the same configuration as those of the image input unit 101 and the display unit 109 in the master display device 100, detailed explanations are omitted.

The synchronization-signal acquiring unit 203 acquires a synchronization signal transmitted from the master display device 100. Furthermore, the configuration of the synchronization-signal acquiring unit 203 may be changed as needed depending on the method for transmitting the synchronization signal. Moreover, the synchronization-signal acquiring unit 203 feeds the acquired synchronization signal to the display controller 205.

The display controller 205 causes the display unit 207 to display the left-eye image and the right-eye image, which correspond to the input image data input via the image input unit 201, in accordance with the synchronization signal fed from the synchronization-signal acquiring unit 203 in a time-division manner so as to be synchronized with the timing indicated by the synchronization signal. Here, the display controller 205 may delay the timing in which the left-eye image and the right-eye image are displayed on the display unit 207 so as to synchronize the timing in which the left-eye image and the right-eye image are displayed with the timing indicated by the synchronization signal. Here, the display unit 207 corresponds to an example of a "slave-side display unit". Further, the display controller 205 corresponds to an example of a "slave-side display controller".

(The Shutter Glasses 300)

Next, the configuration of the shutter glasses 300 is explained. As illustrated in FIG. 4, the shutter glasses 300 include a left-eye shutter 301, a right-eye shutter 303, a synchronization-signal acquiring unit 305, and a shutter controller 307.

When the shutter glasses 300 are worn by the viewer, the left-eye shutter 301 is held in front of the viewer's left eye and is controlled so as to be opened and closed by the shutter controller 307 described later. In the same manner, when the shutter glasses 300 are worn by the viewer, the right-eye shutter 303 is held in front of the viewer's right eye and is controlled so as to be opened and closed by the shutter controller 307 described later.

The synchronization-signal acquiring unit 305 acquires a synchronization signal transmitted from the master display device 100. Furthermore, the configuration of the synchronization-signal acquiring unit 305 may be changed as needed depending on the method for transmitting the synchronization signal. Moreover, the synchronization-signal acquiring unit 305 feeds the acquired synchronization signal to the shutter controller 307.

In accordance with the synchronization signal fed from the synchronization-signal acquiring unit 305, the shutter controller 307 controls the left-eye shutter 301 and the right-eye shutter 303 so as to be opened and closed such that they are synchronized with the timing indicated by the synchronization signal. For example, this control causes the left-eye shutter 301 to be opened and causes the right-eye shutter 303 to be closed in the timing in which the left-eye image is displayed on the display unit 109 of the master display device 100. In the same manner, the right-eye shutter 303 is opened and the left-eye shutter 301 is closed in the timing in which the right-eye image is displayed on the display unit 109 of the master display device 100. That is, the viewer's left eye observes the left-eye image in the timing in which the left-eye image is displayed on the display unit 109, and the viewer's right eye observes the right-eye image in the timing in which the right-eye image is displayed on the display unit 109.

An example of the functional configuration of the medical-information processing system 1 according to the present embodiment has been explained above with reference to FIG. 4.

<3.3. Process>

Next, an example of the flow of the sequential process of the medical-information processing system 1 according to the present embodiment is explained with a focus on, particularly, a process of the master display device 100 and the slave display device 200.

(The Master Display Device 100)

Figure 5:
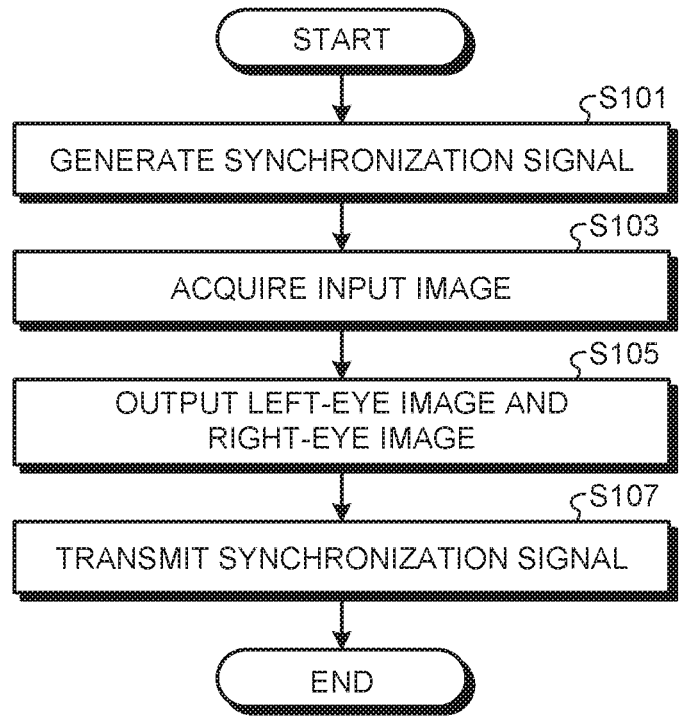
FIG. 5 is a flowchart that illustrates an example of the flow of the sequential process of the medical-information processing system according to the present embodiment.

First, with reference to FIG. 5, the flow of the sequential process of the master display device 100 is explained. FIG. 5 is a flowchart that illustrates an example of the flow of the sequential process of the medical-information processing system 1 according to the present embodiment, and it illustrates the flow of a process of the master display device 100.

The master display device 100 (the synchronization-signal generating unit 103) generates a synchronization signal for displaying the left-eye image and the right-eye image, which correspond to the input image data, in a time-division manner (S101).

Furthermore, image data on the target image to be displayed is input to the master display device 100 via a predetermined input interface (the image input unit 101). Thus, the master display device 100 acquires the image data (S103).

The master display device 100 (the display controller 107) causes the display panel (the display unit 109) to display the left-eye image and the right-eye image, which correspond to the input image data, in a time-division manner in accordance with the generated synchronization signal (S105).

Furthermore, the master display device 100 (the synchronization-signal transmitting unit 105) transmits the generated synchronization signal to the slave display device 200 and the shutter glasses 300 (S107).

(The Slave Display Device 200)

Figure 6:
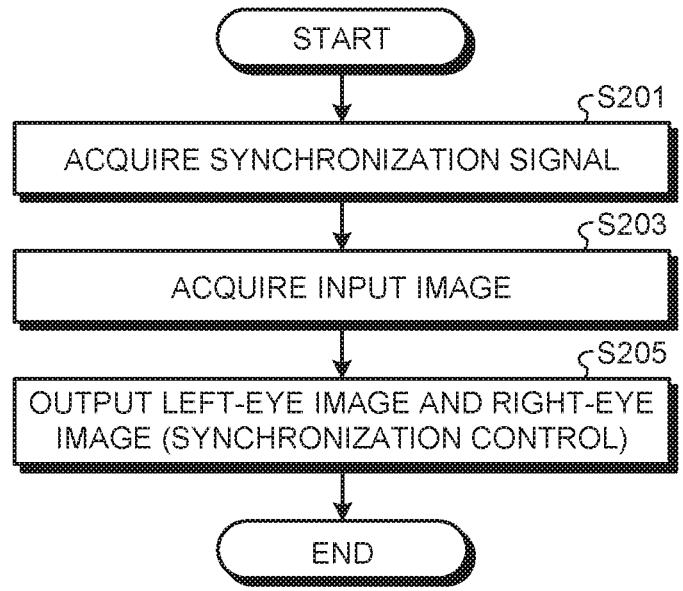
FIG. 6 is a flowchart that illustrates an example of the flow of the sequential process of the medical-information processing system according to the present embodiment.

Next, with reference to FIG. 6, the flow of the sequential process of the master display device 100 is explained. FIG. 6 is a flowchart that illustrates an example of the flow of the sequential process of the medical-information processing system 1 according to the present embodiment, and it illustrates the flow of a process of the slave display device 200.

The slave display device 200 (the synchronization-signal acquiring unit 203) acquires a synchronization signal transmitted from the master display device 100 (S201).

Furthermore, the image data on the target image to be displayed is input to the slave display device 200 via the predetermined input interface (the image input unit 201). Thus, the slave display device 200 acquires the image data (S203).

The slave display device 200 (the display controller 205) causes the display panel (the display unit 207) to display the left-eye image and the right-eye image, which correspond to the input image data, in accordance with the synchronization signal acquired from the master display device 100 in a time-division manner such that they are synchronized with the timing indicated by the synchronization signal. Here, the slave display device 200 may delay the timing in which the left-eye image and the right-eye image are displayed on the display panel so as to synchronize the timing in which the left-eye image and the right-eye image are displayed with the timing indicated by the synchronization signal (S205).

An example of the flow of the sequential process of the medical-information processing system 1 according to the present embodiment has been explained above with reference to FIG. 5 and FIG. 6 with a focus on, particularly, the process of the master display device 100 and the slave display device 200.

<3.4. Modification>

Next, a modification of the medical-information processing system according to the present embodiment is explained.

(Modification 1: An Example of the Configuration of the Slave Display Device)

First, in the modification 1, an example of the configuration of the slave display device 200 is explained. As described above, the slave display device 200 acquires the synchronization signal transmitted from the master display device 100 and causes the display panel (the display unit 207) to display the left-eye image and the right-eye image, which correspond to the input image data, in a time-division manner such that they are synchronized with the timing indicated by the synchronization signal. In the modification 1, an explanation is given of an example of the case where a part related to the synchronization control is configured as an externally connected device among the configurations of the above-described slave display device 200.

Figure 7:
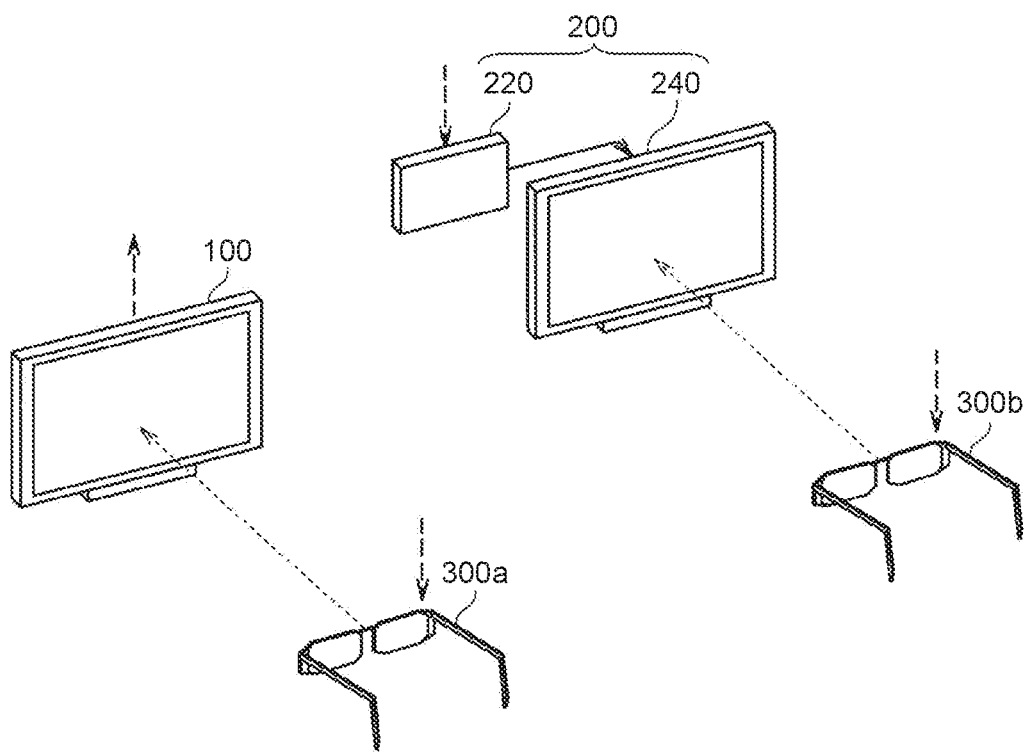
FIG. 7 is an explanatory diagram that illustrates an example of the configuration of a slave display device according to a modification 1.

For example, FIG. 7 is an explanatory diagram that illustrates an example of the configuration of the slave display device 200 according to the modification 1. As illustrated in FIG. 7, the slave display device 200 according to the modification 1 is configured such that a synchronization control device 220 is externally connected to a display device 240.

The display device 240 includes a display panel that corresponds to the display unit 207 illustrated in FIG. 4, and it displays the left-eye image and the right-eye image, which correspond to the input image data, in a time-division manner in display timing based on the control from the synchronization control device 220.

The synchronization control device 220 includes a component that corresponds to the synchronization-signal acquiring unit 203 illustrated in FIG. 4, and it acquires a synchronization signal transmitted from the master display device 100. Furthermore, the synchronization control device 220 controls the timing in which each of the left-eye image and the right-eye image is displayed on the display panel of the display device 240 in accordance with the acquired synchronization signal.

Furthermore, there is no particular limitation on the configuration and the method as long as the timing in which the display device 240 displays each of the left-eye image and the right-eye image on the display panel is controlled in accordance with the synchronization signal acquired by the synchronization control device 220.

In a specific example, the synchronization control device 220 may feed the acquired synchronization signal to the display device 240 so that the display device 240 controls the timing in which each of the left-eye image and the right-eye image is displayed on the display panel. In this case, the display device 240 may control the timing in which each of the left-eye image and the right-eye image, which correspond to the input image data input via the predetermined input interface, is displayed in accordance with the synchronization signal fed from the synchronization control device 220.

Furthermore, in another example, the synchronization control device 220 may control the display timing in which each of the left-eye image and the right-eye image is displayed on the display panel of the display device 240. In this case, the synchronization control device 220 feeds each of the left-eye image and the right-eye image, which correspond to the input image data input via the predetermined input interface, to the display device 240 in a time-division manner so as to be synchronized with the acquired synchronization signal. Moreover, the display device 240 may cause the display panel to display the left-eye image and the right-eye image that are fed from the synchronization control device 220 in a time-division manner.

Further, when the slave display devices 200 are in operation, all the slave display devices 200 do not always need to be configured such that the synchronization control device 220 is externally connected to the display device 240 as in the present modification. For example, as the slave display devices 200, there may be the slave display device 200 according to the above-described embodiment and the slave display device 200 (i.e., the display device 240 having the synchronization control device 220 externally connected thereto) according to the present modification in a mixed manner.

With the above configuration, for example, the existing display device may be operated as the slave display device 200 according to the present disclosure by externally connecting the synchronization control device 220 according to the modification 1. Furthermore, the synchronization control device 220 corresponds to an example of a "medical-image display control device".

An example of the configuration of the slave display device 200 has been explained above with reference to FIG. 7 as the modification 1.

(Modification 2: An Example of the System Configuration)

Next, another example of the system configuration of the medical-information processing system according to the embodiment of the present disclosure is explained as a modification 2. Furthermore, in the following explanation, the medical-information processing system according to the present modification is sometimes referred to as a "medical-information processing system 2" to be distinguished from the medical-information processing system 1 according to the above-described embodiment.

In the above-described embodiment, an explanation is given of an example of the case where the master display device 100 and the slave display device 200 are explicitly distinguished and the master display device 100 is fixedly set. Conversely, according to the present modification, an explanation is given of an example of the medical-information processing system that is configured such that the display device operating as the device that corresponds to the above-described master display device 100 is selectively switched among a plurality of display devices. Furthermore, in the following explanation, the device that corresponds to the above-described master display device 100 is also referred to as the "master device", and the device that corresponds to the slave display device 200 is also referred to as the "slave device".

Figure 8:
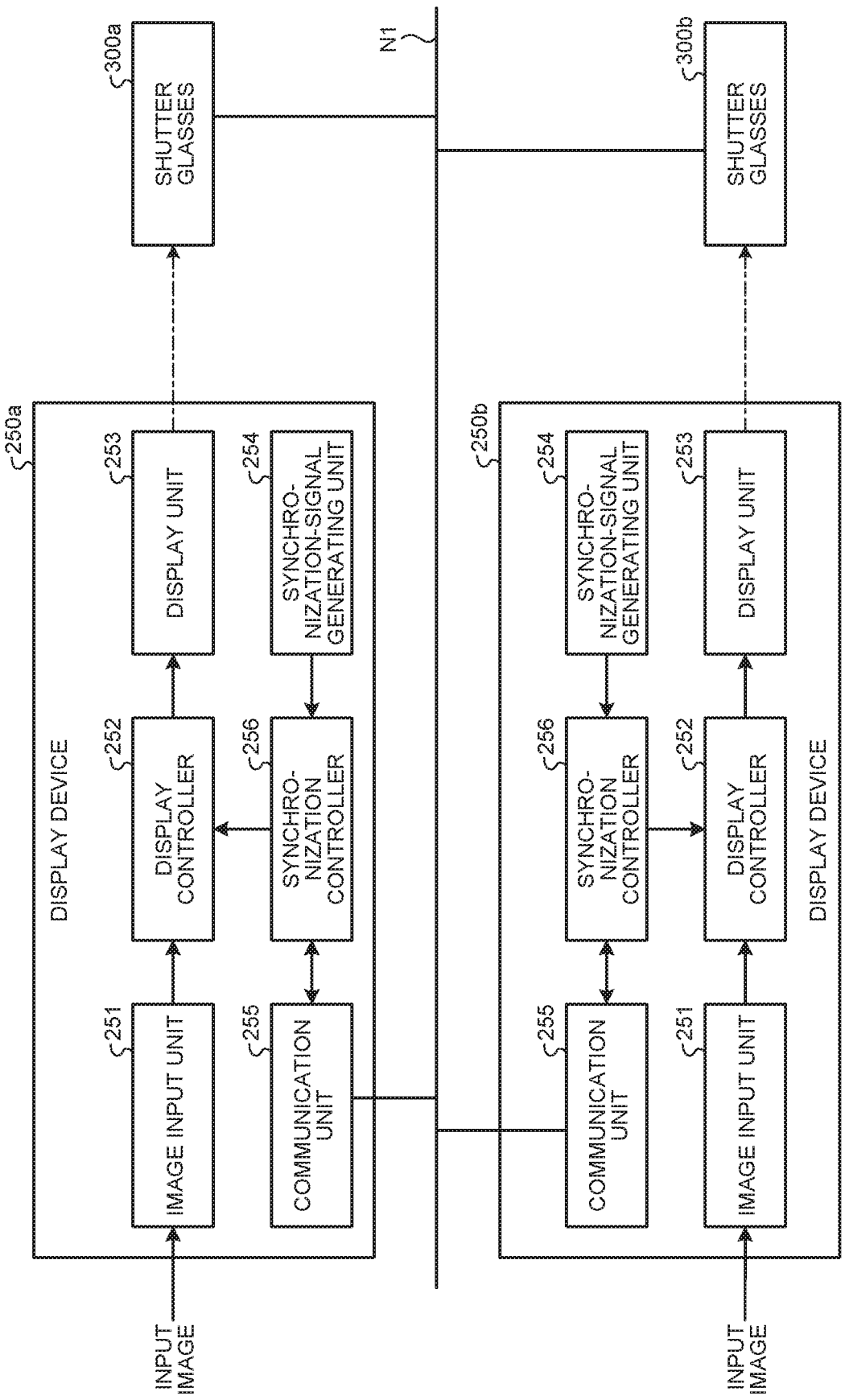
FIG. 8 is a block diagram that illustrates an example of the functional configuration of a medical-information processing system according to a modification 2.

For example, FIG. 8 is a block diagram that illustrates an example of the functional configuration of the medical-information processing system 2 according to the modification 2. As illustrated in FIG. 8, the medical-information processing system 2 according to the present modification includes a plurality of display devices 250 and the plurality of pair of shutter glasses 300. Furthermore, in the example illustrated in FIG. 8, display devices 250a and 250b correspond to the respective display devices 250. Moreover, as illustrated in FIG. 8, both the display devices 250a and 250b have the same configuration. Further, as the configuration of the shutter glasses 300 is the same as that of the shutter glasses 300 (see FIG. 4) according to the above-described embodiment, detailed explanations are omitted.

Furthermore, in the medical-information processing system 2 according to the modification 2, the display devices 250 are configured such that they are capable of transmitting/receiving information to/from each other via a predetermined network. Furthermore, any one of the display devices 250 operates as the master device, and each pair of the shutter glasses 300 is configured to acquire a synchronization signal transmitted from the display device 250 operating as the master device. Furthermore, there is no particular limitation on the method of communications between the display devices 250 and there is also no limitation on the method of transmitting synchronization signals to each pair of the shutter glasses 300 from the display device 250 operating as the master device as long as the above-described condition is satisfied. For example, in the example illustrated in FIG. 8, each of the display devices 250 and each pair of the shutter glasses 300 are configured so as to communicate via a predetermined network N1.

Next, the configuration of the display device 250 is explained. As illustrated in FIG. 8, the display device 250 includes an image input unit 251, a display controller 252, a display unit 253, a synchronization-signal generating unit 254, a communication unit 255, and a synchronization controller 256. Furthermore, as the image input unit 251 and the display unit 253 have substantially the same configuration as those of the image input unit 101 and the display unit 109 in the master display device 100 according to the above-described embodiment or those of the image input unit 201 and the display unit 207 in the slave display device 200, detailed explanations are omitted.

The display controller 252 causes the display unit 253 to display the left-eye image and the right-eye image, which correspond to the input image data input via the image input unit 251, in a time-division manner in accordance with the synchronization signal fed from the synchronization controller 256 described later.

The communication unit 255 is a communication interface for transmitting/receiving various types of information between the display device 250 and the other display device 250 or the shutter glasses 300 via the predetermined network N1. Furthermore, in the following explanation, when a component in the display device 250 transmits/receives information to/from another device (e.g., the other display device 250 or the shutter glasses 300), information is transmitted and received via the communication unit 255 if not otherwise specified.

The synchronization-signal generating unit 254 generates a synchronization signal for displaying, in a time-division manner, the left-eye image and the right-eye image which correspond to the input image data (i.e., a synchronization signal that corresponds to the timing in which each of the left-eye image and the right-eye image is displayed) when the display device 250 operates as the master device. The synchronization-signal generating unit 254 outputs the generated synchronization signal to the synchronization controller 256.

The synchronization controller 256 performs control as to whether the display device 250 operates in any operation mode, either the operation mode in which it operates as the master device (hereafter, also referred to as "master mode") or the operation mode in which it operates as the slave device (hereafter, also referred to as "slave mode"). Furthermore, the synchronization controller 256 feeds a synchronization signal that corresponds to the operation mode to the display controller 252, thereby controlling the timing in which each of the left-eye image and the right-eye image, which correspond to the input image data, is displayed on the display unit 253 in a time-division manner. An operation of the synchronization controller 256 is explained below in further detail.

First, an operation related to mode control by the synchronization controller 256 is explained. The synchronization controller 256 selectively switches the operation mode of the display device 250 between the master mode and the slave mode based on a predetermined condition. In a specific example, when the synchronization controller 256 receives a command for operation as the master device from a predetermined user (e.g., an operator who performs a surgery) via a predetermined input unit (not illustrated), it switches the operation mode of the corresponding display device 250 to the master mode. Furthermore, in another example, the synchronization controller 256 may dynamically switch the operation mode of the corresponding display device 250 to the master mode in accordance with a detection result of a predetermined state by a detecting unit (not illustrated) such as various types of sensors. Furthermore, a specific example of the method of dynamically switching the display device 250 operating as the master device is separately described later.

Furthermore, after the operation mode of the display device 250 is switched to the master mode, the synchronization controller 256 notifies the other display device 250 via the network N1 that the operation mode has been switched to the master mode. In a specific example, if the operation mode of the display device 250a is switched to the master mode, the synchronization controller 256 of the display device 250a notifies the other display device 250 (e.g., the display device 250b) that the operation mode has been switched.

Furthermore, based on the notification from the other display device 250, the synchronization controller 256 recognizes that the operation mode of the other display device 250 has been switched to the master mode. In a specific example, after the operation mode of the display device 250b is switched to the master mode, the synchronization controller 256 of the display device 250a recognizes that the operation mode of the display device 250b has been switched to the master mode based on the notification from the display device 250b. In this case, the synchronization controller 256 of the display device 250a switches the operation mode of the display device 250a to the slave mode. With the above configuration, exclusion control is performed such that only any one of the display devices 250 operates as the master device and the other display device 250 operates as the slave device.

Next, an explanation is given of an operation by the synchronization controller 256 regarding the control on the timing in which each of the left-eye image and the right-eye image, which corresponds to the input image data, is displayed on the display unit 253 in a time-division manner. Furthermore, the operation of the synchronization controller 256 is different in the case of operation in the master mode and operation in the slave mode. Therefore, the operation of the synchronization controller 256 is explained separately for the case of operation in the master mode and the case of operation in the slave mode.

First, the case of operation in the master mode is explained. In this case, the synchronization controller 256 feeds a synchronization signal output from the synchronization-signal generating unit 254 to the display controller 252, thereby controlling the timing in which each of the left-eye image and the right-eye image, which correspond to the input image data, is displayed on the display unit 253 in a time-division manner. Furthermore, the synchronization controller 256 transmits the synchronization signal to the other display device 250 and each pair of the shutter glasses 300 via the network N1.

Next, the case of operation in the slave mode is explained. In this case, the synchronization controller 256 acquires, from the other display device 250, a synchronization signal transmitted from the other display device 250 operating in the master mode via the network N1. Then, the synchronization controller 256 feeds the acquired synchronization signal to the display controller 252. At this time, the display controller 252 may delay the timing in which a left-eye image and a right-eye image are displayed in accordance with the synchronization signal so as to display the left-eye image and the right-eye image on the display unit 253 in synchronization with the synchronization signal.

Furthermore, when the operation mode is switched, the synchronization controller 256 and the display controller 252 may again perform control (i.e., resynchronization) on the timing in which the left-eye image and the right-eye image are displayed in a time-division manner in accordance with the synchronization signal that corresponds to the switched operation mode.

Furthermore, the configuration of the above-described display device 250 is merely an example, and the above-described configuration is not always a limitation. For example, at least a part of the display devices 250 may be configured as an external device that is externally connected. In a more specific example, among the components in the display device 250 illustrated in FIG. 8, a part of the components (e.g., the synchronization-signal generating unit 254, the synchronization controller 256, and the communication unit 255) may be externally connected as a device that corresponds to the synchronization control device 220 with reference to FIG. 7.

An example of the functional configuration of the medical-information processing system 2 according to the modification 2 has been explained above with reference to FIG. 8.

Figure 9:
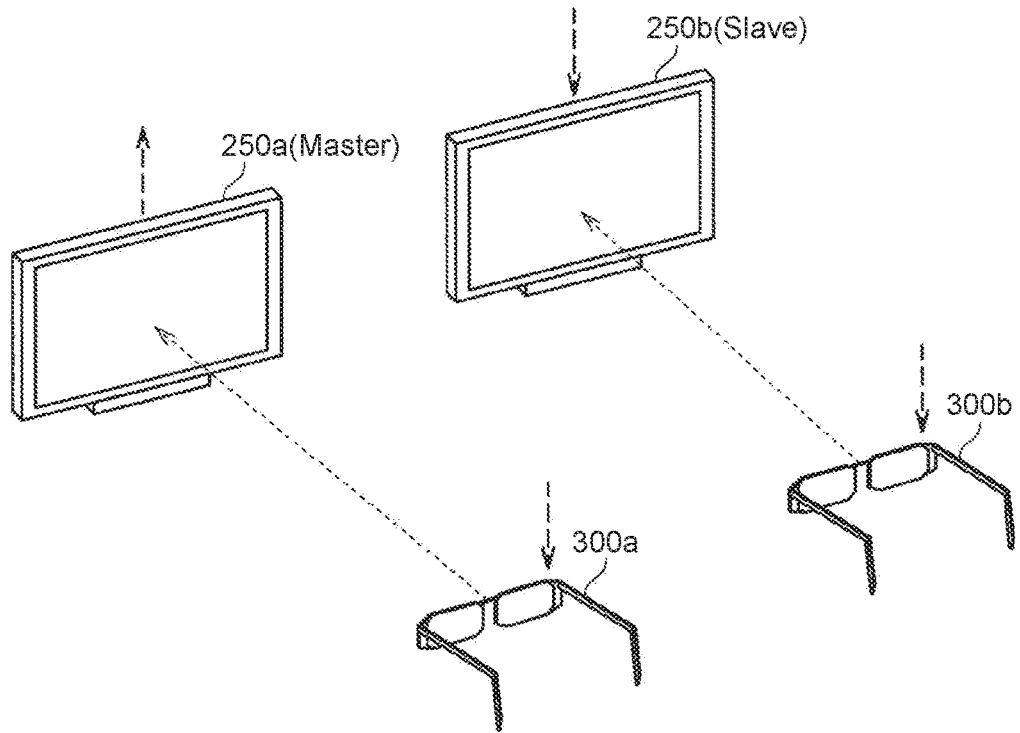
FIG. 9 is an explanatory diagram that illustrates one mode of the operation of the medical-information processing system according to the modification 2.
Figure 10:
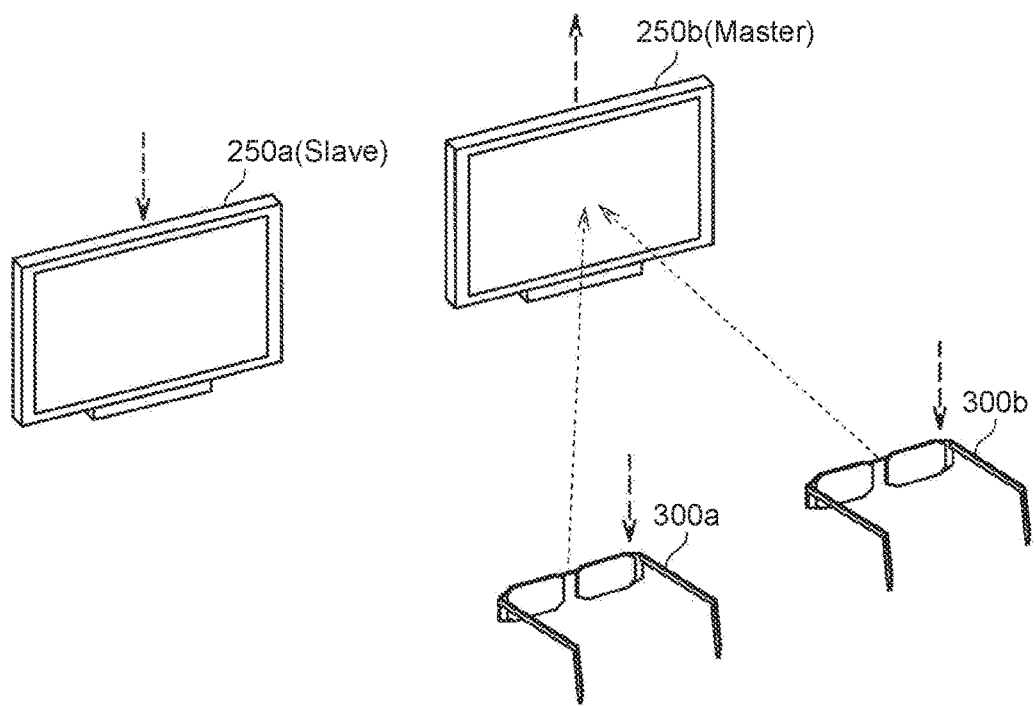
FIG. 10 is an explanatory diagram that illustrates one mode of the operation of the medical-information processing system according to the modification 2.

Next, with reference to FIG. 9 and FIG. 10, an explanation is given of a specific example of the method of dynamically switching the display device 250 operating as the master device. FIG. 9 and FIG. 10 are explanatory diagrams that illustrate one mode of the operation of the medical-information processing system according to the modification 2.

Specifically, FIG. 9 and FIG. 10 illustrate an example of the case where the display device 250 operating as the master device is dynamically switched such that the display device 250, which is the output source of an image viewed by a predetermined viewer such as an operator who performs a surgery, operates as the master device. In FIG. 9 and FIG. 10, the reference numeral 300a denotes the shutter glasses 300 worn by the predetermined viewer such as an operator, and the reference numeral 300b denotes the shutter glasses 300 worn by another viewer other than the operator (that is, the predetermined viewer) such as assistant, anesthetist, or nurse.

First, the example illustrated in FIG. 9 is explained. In the example of the situation illustrated in FIG. 9, the viewer (e.g., operator) wearing the shutter glasses 300a views the image displayed on the display device 250a, and the other viewer wearing the shutter glasses 300b views the image displayed on the display device 250b. In this case, the display device 250a operates as the master device, and it transmits a synchronization signal to the display device 250b and each pair of the shutter glasses 300a and 300b. Specifically, the display device 250b and each pair of the shutter glasses 300a and 300b are operated in synchronization with the timing in which the left-eye image and the right-eye image are displayed on the display device 250a in a time-division manner.

Next, in the example illustrated in FIG. 10, it is assumed that the viewer wearing the shutter glasses 300a turns his/her eyes toward the display device 250b and pays attention to the image displayed on the display device 250b. In this case, the display device 250b recognizes that the viewer wearing the shutter glasses 300a pays attention and, in accordance with a recognition result, switches its operation mode to the master mode. Furthermore, the display device 250b notifies the display device 250a that the operation mode has been switched to the master mode. After receiving the notification, the display device 250a switches the operation mode to the slave mode. Thus, the display device 250b operates as the master device, and the display device 250a operates as the slave device. Furthermore, in the example of the case illustrated in FIG. 10, the display device 250b transmits a synchronization signal to the display device 250a and each pair of the shutter glasses 300a and 300b. That is, the display device 250a and each pair of the shutter glasses 300a and 300b are operated in synchronization with the timing in which the left-eye image and the right-eye image are displayed on the display device 250b in a time-division manner.

An explanation is given above of, as the modification 2, another example of the system configuration of the medical-information processing system according to the embodiment of the present disclosure with reference to FIG. 8 to FIG. 10.

<<4. Application Example>>

Next, an explanation is given of an application example of the medical-information processing system according to the embodiment of the present disclosure. An explanation is given above of an example of the case where the surgical video microscope apparatus is applied as the medical stereoscopic observation apparatus in the medical-information processing system according to the embodiment of the present disclosure. However, the device applied as the medical stereoscopic observation apparatus in the medical-information processing system according to the present embodiment is not always limited to only the surgical video microscope apparatus. Therefore, an explanation is given below of an example of the device that is applicable as the medical stereoscopic observation apparatus in the medical-information processing system according to the present embodiment.

<4.1. First Application Example: Rigid Endoscope Device>

Figure 11:
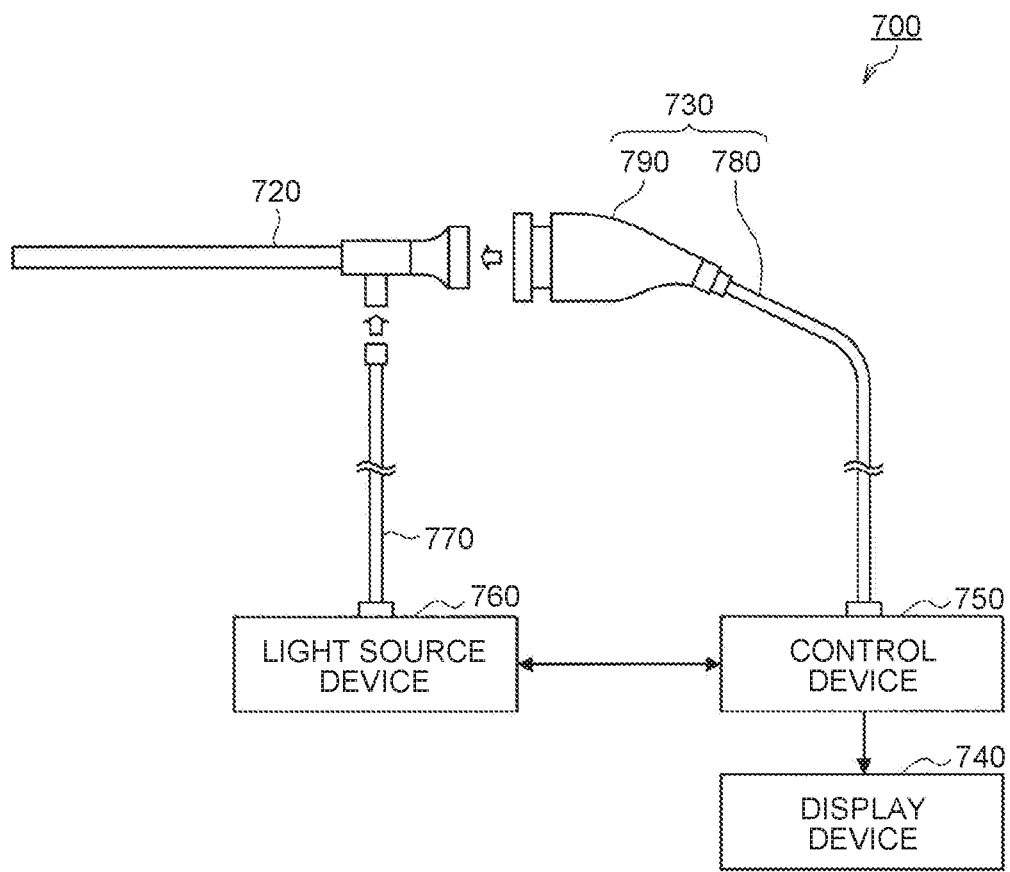
FIG. 11 is an explanatory diagram that illustrates an example of the medical stereoscopic observation apparatus applied to the medical-information processing system according to the present embodiment.
Figure 12:
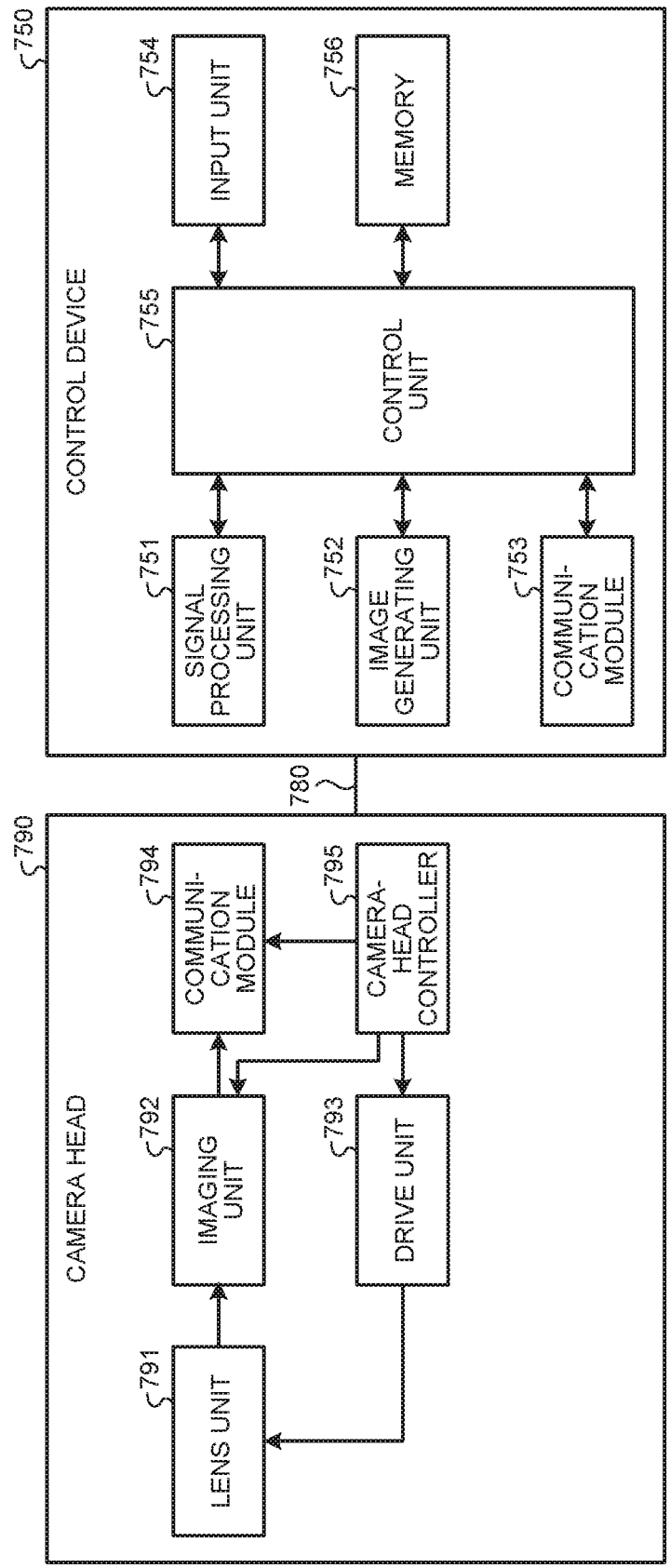
FIG. 12 is an explanatory diagram that illustrates an example of the medical stereoscopic observation apparatus applied to the medical-information processing system according to the present embodiment.

First, with reference to FIG. 11 and FIG. 12, a first application example according to the present embodiment is explained. In this application example, an explanation is given of an example of the case where what is called a rigid endoscope device is applied as the medical stereoscopic observation apparatus in the medical-information processing system according to the present embodiment. For example, FIG. 11 is an explanatory diagram that illustrates an example of the medical stereoscopic observation apparatus applied to the medical-information processing system according to the present embodiment, and it illustrates an example of the schematic configuration of the rigid endoscope device. An endoscope device 700 is a device that is used in the medical field and that observes an object inside the observation target (inside the living body) such as a person. As illustrated in FIG. 11, the endoscope device 700 includes an endoscope 720, an imaging device 730 (medical imaging device), a display device 740, a control device 750 (image processing device), and a light source device 760, and the imaging device 730 and the control device 750 constitute a medical-image acquisition system. Furthermore, in this application example, the endoscope 720 and the imaging device 730 constitute an endoscope device using a rigid endoscope.

The light source device 760 supplies white illumination light for illuminating the inside of the living body to one end of a light guide 770, the end of the light guide 770 being connected to the endoscope 720. One end of the light guide 770 is connected to the light source device 760 in an attachable and detachable manner, and the other end thereof is connected to the endoscope 720 in an attachable and detachable manner. Furthermore, the light guide 770 propagates the light fed from the light source device 760 from one end to the other end, thereby supplying it to the endoscope 720.

The imaging device 730 captures an object image from the endoscope 720 and outputs the capturing result. As illustrated in FIG. 11, the imaging device 730 includes a transmission cable 780, which is a signal transmitting unit, and a camera head 790. According to the first embodiment, the transmission cable 780 and the camera head 790 constitute a medical imaging device.

The endoscope 720 is rigid and has an elongated shape, and it is inserted into the living body. Inside the endoscope 720, an optical system configured by using one or more lenses to collect an object image is disposed. The endoscope 720 outputs the light supplied via the light guide 770 from the distal end thereof and emits it into the living body. Then, the light (object image) emitted into the living body is collected by the optical system (a lens unit 791) in the endoscope 720.

The camera head 790 is connected to the proximal end of the endoscope 720 in an attachable and detachable manner. Furthermore, under the control of the control device 750, the camera head 790 captures the object image collected by the endoscope 720 and outputs an imaging signal during the capturing.

One end of the transmission cable 780 is connected to the control device 750 via a connector in an attachable and detachable manner, and the other end thereof is connected to the camera head 790 via a connector in an attachable and detachable manner. Specifically, the transmission cable 780 is a cable in which a plurality of electric wires (not illustrated) is disposed on the inner side of the outer covering that is the outermost layer. The electric wires are electric wires for transmitting imaging signals output from the camera head 790, control signals output from the control device 750, synchronization signals, clocks, and electric power to the camera head 790.

Under the control of the control device 750, the display device 740 displays images (i.e., medical images) generated by the control device 750. The display device 740 preferably has the display unit of equal to or more than 55 inches so as to easily obtain a sense of immersion during observation; however, this is not a limitation.

The control device 750 processes imaging signals input from the camera head 790 via the transmission cable 780 and outputs image signals to the display device 740, and it controls operations of the camera head 790 and the display device 740 in an integrated manner. Furthermore, the detailed configuration of the control device 750 is described later.

Next, the configurations of the imaging device 730 and the control device 750 are explained. FIG. 12 is an explanatory diagram that illustrates an example of the medical stereoscopic observation apparatus applied to the medical-information processing system according to the present embodiment, and it is a block diagram that illustrates the configurations of the imaging device 730 and the control device 750. Furthermore, in FIG. 12, the connector that allows the camera head 790 and the transmission cable 780 to be attached to and detached from each other is not illustrated.

The configuration of the control device 750 and the configuration of the camera head 790 are explained below in this order. Furthermore, as the configuration of the control device 750, the relevant part according to the present disclosure is principally explained below. As illustrated in FIG. 12, the control device 750 includes a signal processing unit 751, an image generating unit 752, a communication module 753, an input unit 754, a control unit 755, and a memory 756. Furthermore, the control device 750 may be provided with a power source unit (not illustrated), or the like, which generates a power-supply voltage for driving the control device 750 and the camera head 790, supplies it to each unit of the control device 750, and supplies it to the camera head 790 via the transmission cable 780.

The signal processing unit 751 performs signal processing such as noise removal or A/D conversion as needed on imaging signal output from the camera head 790, thereby outputting digital imaging signals (pulse signals) to the image generating unit 752.

Furthermore, the signal processing unit 751 generates clocks and synchronization signals for the imaging device 730 and the control device 750. Synchronization signals (e.g., synchronization signals for giving a command for the imaging timing of the camera head 790) and clocks (e.g., clocks for serial communication) for the imaging device 730 are transmitted to the imaging device 730 via an undepicted line and, based on the synchronization signal or the clock, the imaging device 730 is driven.

The image generating unit 752 generates display image signals displayed by the display device 740 based on imaging signals input from the signal processing unit 751. The image generating unit 752 performs predetermined signal processing on an imaging signal to generate a display image signal including an object image. Here, the image processing includes various types of image processing such as interpolation processing, color correction processing, color enhancement processing, and outline enhancement processing. The image generating unit 752 outputs generated image signals to the display device 740.

The communication module 753 outputs signals from the control device 750, including control signals transmitted from the control unit 755 as described later, to the imaging device 730. Furthermore, signals from the imaging device 730 are output to the control device 750. That is, the communication module 753 is a relay device that collectively outputs signals, from each unit of the control device 750, to be output to the imaging device 730 due to, for example, parallel-serial conversion and that outputs signals, input from the imaging device 730, to each unit of the control device 750 by sorting due to, for example, serial-parallel conversion.

The input unit 754 is implemented by using a user interface such as keyboard, mouse, or touch panel, and it receives input of various types of information.

The control unit 755 controls driving of each component including the control device 750 and the camera head 790, controls input/output of information to/from each component, and the like. The control unit 755 generates control signals by referring to communication information data (e.g., communication format information) recorded in the memory 756 and transmits the generated control signal to the imaging device 730 via the communication module 753. Furthermore, the control unit 755 outputs control signals to the camera head 790 via the transmission cable 780.

The memory 756 is implemented by using a semiconductor memory such as flash memory or DRAM (Dynamic Random Access Memory), and it stores communication information data (e.g., communication format information). Furthermore, the memory 756 may store various programs, or the like, performed by the control unit 755.

Furthermore, the signal processing unit 751 may include an AF processing unit that outputs a predetermined AF evaluation value of each frame based on an imaging signal of an input frame and an AF calculating unit that performs an AF calculation process to select the fame, the focus lens position, or the like, that is most suitable as the focus position based on the AF evaluation value of each frame from the AF processing unit.

Furthermore, the signal processing unit 751, the image generating unit 752, the communication module 753, and the control unit 755 described above are implemented by using a general-purpose processor such as a CPU (Central Processing Unit) including an internal memory (not illustrated) having a program recorded therein or a dedicated processor such as various arithmetic circuits to perform a specific function, such as an ASIC (Application Specific Integrated Circuit). Furthermore, it may be configured by using an FPGA (Field Programmable Gate Array: not illustrated) that is one type of programmable integrated circuit. When it is configured by using an FPGA, a memory storing configuration data may be provided, and an FPGA, which is a programmable integrated circuit, may be configured with configuration data read from the memory.

Next, the relevant part according to the present invention is principally explained as the configuration of the camera head 790. As illustrated in FIG. 12, the camera head 790 includes the lens unit 791, an imaging unit 792, a drive unit 793, a communication module 794, and a camera-head controller 795.

The lens unit 791 is configured by using one or more lenses, and it focuses the object image collected by the endoscope 720 onto the imaging surface of the imaging element included in the imaging unit 792. The one or more lenses are configured so as to move along the optical axis. Furthermore, the lens unit 791 is provided with an optical zoom mechanism (not illustrated) that changes the angle of view or a focus mechanism that changes the focal point by moving the one or more lenses. Moreover, in addition to the optical zoom mechanism and the focus mechanism, the lens unit 791 may be provided with a diaphragm mechanism or an optical filter (e.g., a filter that cuts infrared light) that is attachable and detachable along the optical axis.

The imaging unit 792 captures the object under the control of the camera-head controller 795. The imaging unit 792 is configured by using two imaging elements, such as CCD (Charge Coupled Device) or CMOS (Complementary Metal Oxide Semiconductor), which receives the object image formed by the lens unit 791 and converts it into an electric signal, and a prism that disperses observation light and causes the dispersed light to enter each of the two imaging elements. In the case of the CCD, for example, a sensor chip, or the like, includes a signal processing unit (not illustrated) that conducts signal processing (A/D conversion, or the like) on an electric signal (analog signal) from the imaging element and outputs an imaging signal. In the case of the CMOS, for example, the imaging element includes a signal processing unit that conducts signal processing (A/D conversion, or the like) on an electric signal (analog), which is converted from light, and outputs an imaging signal. The configuration of the imaging unit 792 is described later.

The drive unit 793 includes a driver that operates the optical zoom mechanism or the focus mechanism to change the angle of view or the focus position of the lens unit 791 under the control of the camera-head controller 795.

The communication module 794 outputs signals transmitted from the control device 750 to each unit of the camera head 790, such as the camera-head controller 795. Furthermore, the communication module 794 converts information regarding the current state of the camera head 790, or the like, into a signal format that corresponds to a predetermined transmission system and outputs the converted signal to the control device 750 via the transmission cable 780. That is, the communication module 794 is a relay device that sorts signals input from the control device 750 or the transmission cable 780 due to, for example, serial-parallel conversion and outputs it to each unit of the camera head 790 and that collectively outputs signals, from each unit of the camera head 790, to be output to the control device 750 or the transmission cable 780 due to for example parallel-serial conversion.

The camera-head controller 795 controls the overall operation of the camera head 790 in accordance with a drive signal input via the transmission cable 780 or a command signal, or the like, output from an operating unit, such as a switch that is provided and exposed on the outer surface of the camera head 790, due to the user's operation on the operating unit. Furthermore, the camera-head controller 795 outputs information about the current state of the camera head 790 to the control device 750 via the transmission cable 780.

Furthermore, the drive unit 793, the communication module 794, and the camera-head controller 795 described above are implemented by using a general-purpose processor such as a CPU (Central Processing Unit) including an internal memory (not illustrated) having a program recorded therein or a dedicated processor such as various arithmetic circuits to perform a specific function, such as an ASIC (Application Specific integrated Circuit). Furthermore, it may be configured by using an FPGA that is one type of programmable integrated circuit. When it is configured by using an FPGA, a memory storing configuration data may be provided, and an FPGA, which is a programmable integrated circuit, may be configured with configuration data read from the memory.

Furthermore, the camera head 790 or the transmission cable 780 may be provided with a signal processing unit that executes signal processing on imaging signals generated by the communication module 794 or the imaging unit 792. Furthermore, an imaging clock for driving the imaging unit 792 and a drive clock for driving the drive unit 793 may be generated based on the reference clock generated by an oscillator (not illustrated) disposed in the camera head 790 and output to each of the imaging unit 792 and the drive unit 793, and timing signals for various processes in the imaging unit 792, the drive unit 793, and the camera-head controller 795 may be generated based on synchronization signals input from the control device 750 via the transmission cable 780 and output to each of the imaging unit 792, the drive unit 793, and the camera-head controller 795. Furthermore, the camera-head controller 795 may be provided in not the camera head 790 but the transmission cable 780 or the control device 750.

Furthermore, the configuration including the lens unit 791, the imaging unit 792, and the drive unit 793 described above may correspond to the imaging device 290a or the imaging device 290b explained with reference to FIG. 3. Moreover, the display device 740 may correspond to the master display device 100 or the slave display device 200 explained above with reference to FIG. 3.

An explanation is given above of an example of the case where what is called a rigid endoscope device is applied as the medical stereoscopic observation apparatus in the medical-information processing system according to the present embodiment with reference to FIG. 11 and FIG. 12.

<4.2. Second Application Example: Flexible Endoscope Device>

Figure 13:
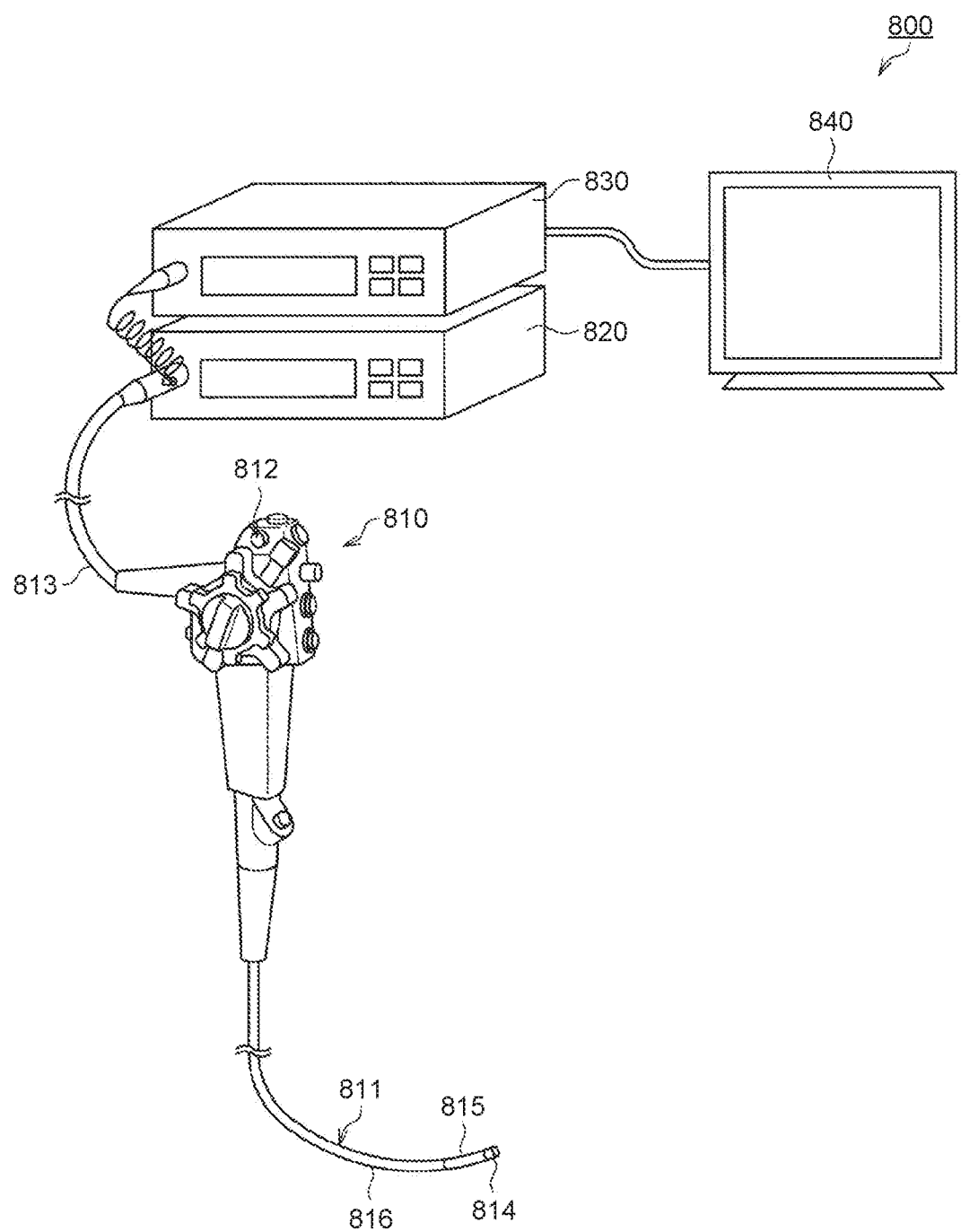
FIG. 13 is an explanatory diagram that illustrates another example of the medical stereoscopic observation apparatus applied to the medical information processing system according to the present embodiment.

Next, with reference to FIG. 13, a second application example according to the present embodiment is explained. In this application example, an explanation is given of an example of the case where what is called a flexible endoscope device is applied as the medical stereoscopic observation apparatus in the medical-information processing system according to the present embodiment. FIG. 13 is an explanatory diagram that illustrates another example of the medical stereoscopic observation apparatus applied to the medical-information processing system according to the present embodiment, and it illustrates an example of the schematic configuration of the flexible endoscope device.

In the above-described first application example, the endoscope device 700 using the rigid endoscope is explained as the endoscope 720; however, this is not a limitation, and the endoscope 720 may be an endoscope device using a flexible endoscope. In the second application example according to the present embodiment, an explanation is given of an example of the case where an imaging unit is provided at the distal end of an insertion unit of the flexible endoscope.

An endoscope device 800 includes: an endoscope 810 that inserts an insertion unit 811 into the subject to capture an in-vivo image of the observed region and generate an electric signal; a light source device 820 that generates illumination light to be output from the distal end of the endoscope 810; a control device 830 that performs predetermined image processing on an electric signal acquired by the endoscope 810 and controls the overall operation of the endoscope device 800 in an integrated manner; and a display device 840 that displays an in-vivo image on which a processor unit has performed image processing. The endoscope device 800 inserts the insertion unit 811 into the subject such as patient to acquire an in-vivo image of the subject.

The endoscope 810 includes: the insertion unit 811 that has flexibility and has an elongated shape; an operating unit 812 that is connected to the proximal end side of the insertion unit 811 and that receives input of various types of operating signals; and a universal code 813 that extends from the operating unit 812 in a direction different from the direction in which the insertion unit 811 extends and that has various built-in cables connected to the light source device 820 and the control device 830.

The insertion unit 811 includes: a distal end portion 814 that has the imaging unit according to the present application example built in; a curved portion 815 that is composed of a plurality of curved pieces and is curved in a flexible manner; and an elongated flexible tube portion 816 that is connected to the proximal end side of the curved portion 815 and that has flexibility.

Furthermore, the imaging unit provided at the distal end portion 814 may correspond to, for example, the imaging device 290a or the imaging device 290b explained with reference to FIG. 3. Furthermore, the display device 840 may correspond to, for example, the master display device 100 or the slave display device 200 explained above with reference to FIG. 3.

With reference to FIG. 13, an explanation has been given above of an example of the case where what is called the flexible endoscope device is applied as the medical stereoscopic observation apparatus in the medical-information processing system according to the present embodiment.

Furthermore, the above-described first and second application examples are merely position application examples of the medical stereoscopic observation apparatus according to the present embodiment, and it is obvious that they are not limitations on applications of the medical stereoscopic observation apparatus.

<<5. Hardware Configuration>>

Figure 14:
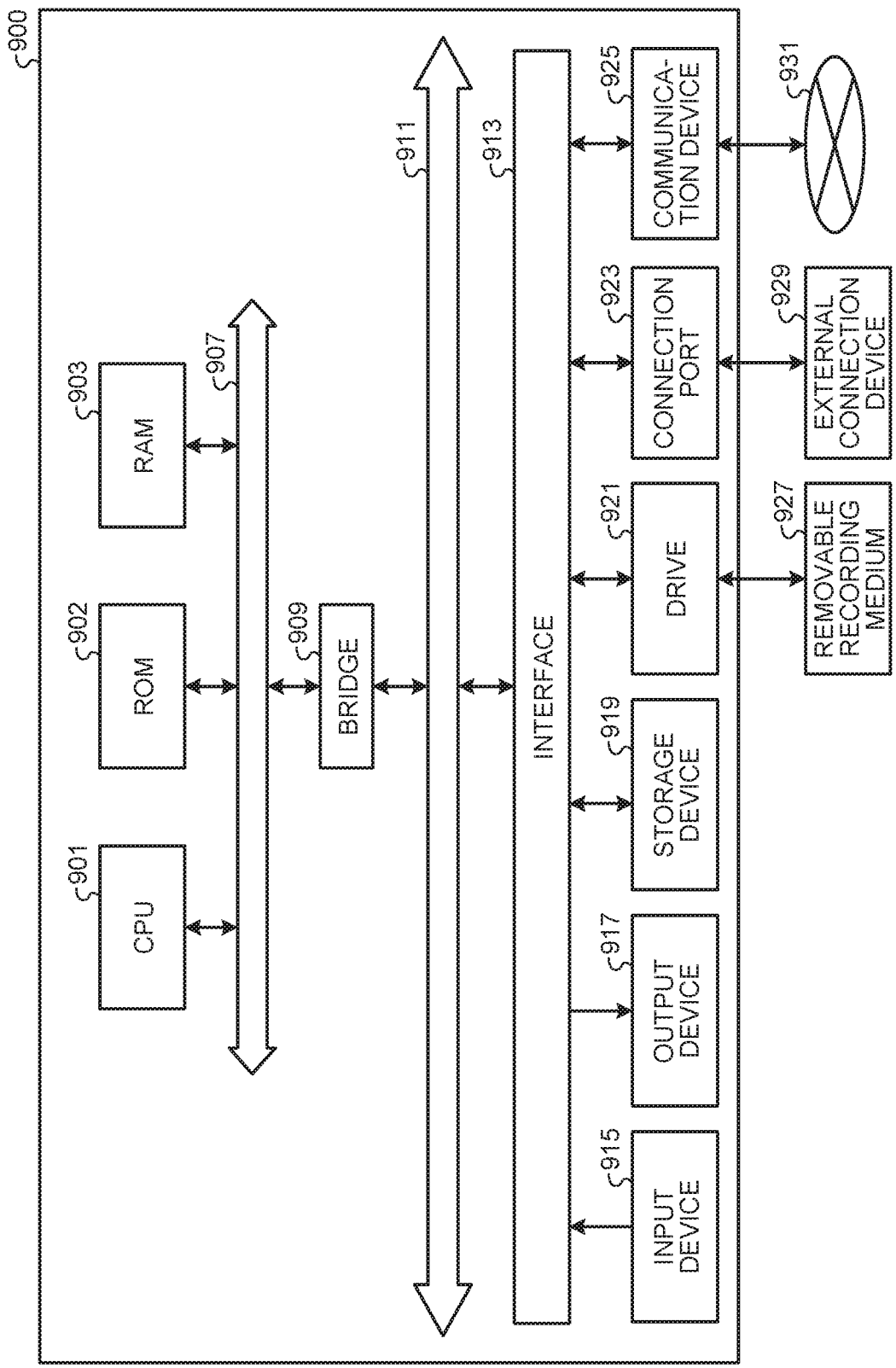
FIG. 14 is a functional block diagram that illustrates a configuration example of the hardware configuration of an information processing apparatus included in the medical-information processing system according to the embodiment of the present disclosure.

Next, with reference to FIG. 14, the hardware configuration of an information processing apparatus 900 included in the medical-information processing system according to the present embodiment is explained in detail. FIG. 14 is a functional block diagram that illustrates a configuration example of the hardware configuration of the information processing apparatus 900 included in the medical-information processing system according to the embodiment of the present disclosure.

The information processing apparatus 900 included in the medical stereoscopic observation system according to the present embodiment principally includes a CPU 901, a ROM 903, and a RAM 905. Furthermore, the information processing apparatus 900 includes a host bus 907, a bridge 909, an external bus 911, an interface 913, an input device 915, an output device 917, a storage device 919, a drive 921, a connection port 923, and a communication device 925.

The CPU 901 functions as an arithmetic processing device and a control device and, in accordance with various programs stored in the ROM 903, the RAM 905, the storage device 919, or a removable recording medium 927, controls all or part of the operation of the information processing apparatus 900. The ROM 903 stores programs, calculation parameters, and the like, used by the CPU 901. The RAM 905 temporarily stores programs used by the CPU 901, parameters changed as needed during execution of a program, and the like. They are connected to one another via the host bus 907 that is formed of an internal bus such as a CPU bus. Furthermore, the display controller 107 and the display controller 205 described above with reference to FIG. 4 may be implemented by the CPU 901.

The host bus 907 is connected to an external bus 911, such as PCI (Peripheral Component Interconnect/Interface) bus via the bridge 909. Furthermore, the eternal bus 911 is coupled to the input device 915, the output device 917, the storage device 919, the drive 921, the connection port 923, and the communication device 925 via the interface 913.

The input device 915 is an operating means operated by the user, such as mouse, keyboard, touch panel, button, switch, lever, or pedal. Also, the input device 915 may be a remote control means (what is called a remote controller) that uses, for example, infrared light or other radio waves, or it may be an external connection device 929 such as a mobile phone or PDA, which corresponds to operation of the information processing apparatus 900. Moreover, for example, the input device 915 is composed of an input control circuit that generates an input signal based on information input by the user using the above-described operating means and outputs it to the CPU 901. The user of the information processing apparatus 900 operates the input device 915 so as to input various types of data to the information processing apparatus 900 and give a command for a processing operation.

The output device 917 is composed of a device that is capable of notifying a user of acquired information in a visual or auditory way. This kind of device is a display device such as CRT display device, liquid crystal display device, plasma display device, EL display device, or lamp, a sound output device such as speaker or headphones, a printer device, or the like. The output device 917 outputs, for example, a result obtained during various types of processing performed by the information processing apparatus 900. Specifically, the display device displays a result obtained during various types of processing performed by the information processing apparatus 900 as a text or image. Furthermore, the sound output device converts an audio signal formed of reproduced audio data or sound data into an analog signal and outputs it. For example, the display unit 109 and the display unit 207 described above with reference to FIG. 4 are implemented by the output device 917.

The storage device 919 is a data storage device that is configured as an example of the storage unit of the information processing apparatus 900. The storage device 919 is configured with, for example, a magnetic storage device such as HDD (Hard Disk Drive), a semiconductor storage device, an optical storage device, or a magnetooptical storage device. The storage device 919 stores programs, various types of data, and the like, executed by the CPU 901.

The drive 921 is a reader/writer for a recording medium, and it is built in or externally connected to the information processing apparatus 900. The drive 921 reads information recorded in the removable recording medium 927, such as magnetic disk, optical disk, magnetic optical disk, or semiconductor memory, which is attached thereto, and outputs it to the RAM 905. Furthermore, the drive 921 is capable of writing records in the removable recording medium 927, such as magnetic disk, optical disk, magnetic optical disk, or semiconductor memory, which is attached thereto. The removable recording medium 927 is, for example, DVD media, HD-DVD media, or Blu-ray (registered trademark) media. Moreover, the removable recording medium 927 may be compact flash (registered trademark) (CF: CompactFlash), flash memory, or SD memory card (Secure Digital memory card). Furthermore, the removable recording medium 927 is, for example, an IC card (Integrated Circuit card) having a non-contact type IC chip installed therein or an electronic device.

The connection port 923 is a port for direct connection to the information processing apparatus 900. Examples of the connection port 923 include a USB (Universal Serial Bus) port, an IEEE1394 port, or an SCSI (Small Computer System Interface) port. Other examples of the connection port 923 include an RS-232C port, an optical audio terminal, or an HDMI (registered trademark) (High-Definition Multimedia Interface) port. By connecting the external connection device 929 to the connection port 923, the information processing apparatus 900 directly acquires various types of data from the external connection device 929 or provides the external connection device 929 with various types of data. For example, the image input unit 101 and the image input unit 201 described above with reference to FIG. 4 may be implemented by the connection port 923.

The communication device 925 is, for example, a communication interface formed of a communication device, or the like, for connecting to a communication network (network) 931. The communication device 925 is, for example, a communication card for a wired or wireless LAN (Local Area Network), Bluetooth (registered trademark), or WUSB (Wireless USB). Furthermore, the communication device 925 may be an optical communication router, ADSL (Asymmetric Digital Subscriber line)) router, or modem for various types of communications, or the like. For example, the communication device 925 is capable of transmitting and receiving signals, and the like, in accordance with a predetermined protocol such as TCP/IP via the Internet or with other communication devices. Furthermore, the communication network 931 connected to the communication device 925 is configured with a network, or the like, connected with a wired line or with radio waves, and it may be, for example, the Internet, LAN for one's home, infrared communication, radio wave communication, or satellite communication. For example, the synchronization-signal transmitting unit 105 and the synchronization-signal acquiring unit 203 described above with reference to FIG. 4 may be implemented by the communication device 925.

An explanation has been given above of an example of the hardware configuration that enables implementation of the function of the information processing apparatus 900 included in the medical-information processing system according to the embodiment of the present disclosure. Each of the above-described components may be configured by using a general-purpose member or may be configured by using the hardware specialized for the function of each component. Therefore, the used hardware configuration may be changed as needed in accordance with the technical level of the time when the present embodiment is implemented. Furthermore, although not illustrated in FIG. 14, it is obvious that various configurations are provided corresponding to the information processing apparatus 900 (i.e., the surgical video microscope apparatus or the image processing device) included in the medical-information processing system.

Furthermore, a computer program for performing each function of the information processing apparatus 900 included in the medical-information processing system according to the above-described embodiment may be configured and installed in a personal computer, or the like. Moreover, a recording medium storing such a computer program and readable by a computer may be also provided. The recording medium is, for example, magnetic disk, optical disk, magnetic optical disk, or flash memory. Furthermore, the above-described computer program may be distributed via for example a network without using any recording medium. Further, there is no particular limitation on the number of computers for executing the computer program. For example, the computer program may be executed by a plurality of computers (e.g., a plurality of servers) in cooperation with each other.

<<6. Conclusion>>

As described above, the medical-information processing system according to the present embodiment includes multiple devices that are explained as the master display device 100, the slave display device 200, and the display device 250; any of the devices operates as a master device, and other devices operate as slave devices. Based on this configuration, the master device controls the corresponding display unit so as to display a left-eye image and a right-eye image in a time-division manner and transmits a synchronization signal that corresponds to the timing in which the left-eye image and the right-eye image are displayed. Furthermore, the slave device acquires the synchronization signal transmitted from the master device and, based on the acquired synchronization signal, controls the corresponding display unit so as to display the left-eye image and the right-eye image.

Furthermore, there is no particular limitation on the type of synchronization signals and the method for transmitting the synchronization signals as long as the slave device acquires the synchronization signals transmitted from the master device. For example, the master device may distribute a synchronization signal to the peripheral slave device through a wireless communication path without designating a transmission destination. Furthermore, the master device may designate a slave device as the transmission destination and transmit a synchronization signal to the slave device through a wireless communication path. Moreover, in another example, the master device may transmit a synchronization signal by using infrared signals, or the like.

With the above configuration, the medical-information processing system according to the present embodiment may minimize the delay in displaying an image on the display device operating as the master device. Furthermore, based on the above assumption, in the medical-information processing system according to the present embodiment, the operations of the display device operating as a slave device and the shutter glasses used by each viewer may be synchronized with the operation of the display device operating as the master device. Therefore, in the circumstance where a certain viewer views an image displayed on each of the display devices through the shutter glasses worn by him/herself, the viewer is capable of viewing a three-dimensional image without fail. Moreover, in the circumstance where multiple viewers view an image displayed on each of the display devices through the shutter glasses worn by themselves, each of the viewers is capable of viewing a three-dimensional image without fail.

Although a preferred embodiment of the present disclosure has been explained above in detail with reference to the accompanying drawings, the technical scope of the present disclosure is not limited to the embodiment. It is obvious that a person skilled in the art of the present disclosure may arrive at various changes or modifications within the scope of the technical idea described in claims, and it is obviously understood that they also belong to the technical scope of the present disclosure.

Furthermore, the advantageous effect described in this description is merely for explanation or illustration, and it is not a limitation. That is, in addition to the above-described advantageous effect or instead of the above-described advantageous effect, the technology according to the present disclosure may produce other advantageous effects that are apparent to those skilled in the art from the explanation in this description.

Furthermore, the following configuration also belongs to the technical scope of the present disclosure.

(1) A medical-image display control device includes: a display controller that controls a medical image so as to be displayed on a slave-side display unit; and an acquiring unit that acquires, from another device including a master-side display unit different from the slave-side display unit, a synchronization signal that corresponds to timing in which the other device displays a left-eye image and a right-eye image forming a medical image on the master-side display unit, wherein the display controller controls a left-eye image and a right-eye image forming a medical image so as to be displayed on the slave-side display unit in a time-division manner in accordance with the synchronization signal acquired.

(2) The medical-image display control device according to (1) described above, wherein the display controller delays display of a left-eye image and a right-eye image forming a medical image on the slave-side display unit in accordance with the synchronization signal, thereby synchronizing timing in which the left-eye image and the right-eye image are displayed with timing in which the other device causes the master-side display unit to display a left-eye image and a right-eye image forming a medical image.

(3) The medical-image display control device according to (1) or (2) described above, including the slave-side display unit.

(4) The medical-image display control device according to (1) or (2) described above, wherein the display controller feeds the acquired synchronization signal to a device including the slave-side display unit, thereby controlling a left-eye image and a right-eye image forming a medical image so as to be displayed on the slave-side display unit in a time-division manner in accordance with the synchronization signal.

(5) The medical-image display control device according to any one of (1) to (4) described above, including a transmitting unit that transmits, to another device, a synchronization signal that corresponds to timing in which a left-eye image and a right-eye image forming a medical image are displayed on the slave-side display unit in a time-division manner according to a predetermined condition.

(6) A medical-image display device including: a display unit; a display controller that controls a left-eye image and a right-eye image forming a medical image so as to be displayed on the display unit in a time-division manner; and a transmitting unit that transmits a synchronization signal that corresponds to timing in which a left-eye image and a right-eye image forming a medical image are displayed on the display unit.

(7) A medical-information processing system including a plurality of devices, wherein any device among the devices operates as a master device, and another device that is different from the master device operates as a slave device, the master device controls a left-eye image and a right-eye image forming a medical image so as to be displayed on a master-side display unit in a time-division manner, and transmits a synchronization signal that corresponds to timing in which the left-eye image and the right-eye image are displayed, and the slave device acquires the synchronization signal and controls a left-eye image and a right-eye image forming a medical image so as to be displayed in a time-division manner on a slave-side display unit different from the master-side display unit in accordance with the synchronization signal.

(8) The medical-information processing system according to described above, wherein the master device includes: the master-side display unit; a master-side display controller that controls a left-eye image and a right-eye image forming a medical image so as to be displayed on the master-side display unit in a time-division manner; and a transmitting unit that transmits the synchronization signal, and the slave device includes: an acquiring unit that acquires the synchronization signal; and a slave-side display controller that controls a left-eye image and a right-eye image forming a medical image so as to be displayed on the slave-side display unit in a time-division manner in accordance with the synchronization signal acquired.

(9) The medical-information processing system according to (7) described above, wherein the master device is selectively switched to any device among the devices according to a predetermined condition.

(10) The medical-information processing system according to (9) described above, wherein the master device is dynamically switched in accordance with a display unit that is an output source of a medical image to be viewed by a predetermined viewer.

(11) The medical-information processing system according to (9) or (10) described above, wherein, when a device operating as the slave device is switched so as to operate as the master device, a device having operated as the master device before the switching operates as a slave device after the switching.

(12) The medical-information processing system according to any one of (7) to (11) described above, including shutter glasses including a left-eye shutter and a right-eye shutter, wherein the shutter glasses control each of the left-eye shutter and the right-eye shutter so as to be opened and closed in accordance with the synchronization signal.

(13) The medical-information processing system according to any one of (7) to (12) described above, including a medical capturing unit that captures an image of a diseased site by using a predetermined imaging unit, wherein the master device causes the master-side display unit to display a left-eye image and a right-eye image forming a medical image that corresponds to an imaging result of the diseased site by the imaging unit in a time-division manner.

(14) A medical-image display control method causing a computer to execute: controlling a medical image so as to be displayed on a slave-side display unit; acquiring, from another device including a master-side display unit different from the slave-side display unit, a synchronization signal that corresponds to timing in which the other device displays a left-eye image and a right-eye image forming a medical image on the master-side display unit; and displaying a left-eye image and a right-eye image forming a medical image so as to be displayed on the slave-side display unit in a time-division manner in accordance with the synchronization signal acquired.

(15) A medical-image display control method causing a computer to execute: controlling a left-eye image and a right-eye image forming a medical image so as to be displayed on a predetermined display unit in a time-division manner; and transmitting a synchronization signal that corresponds to timing in which a left-eye image and a right-eye image forming a medical image are displayed on the display unit.

REFERENCE SIGNS LIST

1 MEDICAL-INFORMATION PROCESSING SYSTEM
100 MASTER DISPLAY DEVICE
101 IMAGE INPUT UNIT
103 SYNCHRONIZATION-SIGNAL GENERATING UNIT
105 SYNCHRONIZATION-SIGNAL TRANSMITTING UNIT
107 DISPLAY CONTROLLER
109 DISPLAY UNIT
200 SLAVE DISPLAY DEVICE
201 IMAGE INPUT UNIT
203 SYNCHRONIZATION-SIGNAL ACQUIRING UNIT

205 DISPLAY CONTROLLER
207 DISPLAY UNIT
220 SYNCHRONIZATION CONTROL DEVICE
290 IMAGING DEVICE
300 SHUTTER GLASSES
301 LEFT-EYE SHUTTER
303 RIGHT-EYE SHUTTER
305 SYNCHRONIZATION-SIGNAL ACQUIRING UNIT
307 SHUTTER CONTROLLER
2 MEDICAL-INFORMATION PROCESSING SYSTEM
250 DISPLAY DEVICE
251 IMAGE INPUT UNIT
252 DISPLAY CONTROLLER
253 DISPLAY UNIT
254 SYNCHRONIZATION-SIGNAL GENERATING UNIT
255 COMMUNICATION UNIT
256 SYNCHRONIZATION CONTROLLER

The invention claimed is:

1. A medical-image display control device comprising:
circuitry configured to
control a medical image so as to be displayed on a slave-side display;
acquire, from another device including a master-side display different from the slave-side display, a synchronization signal that corresponds to timing in which the other device displays a left-eye image and a right-eye image forming a medical image on the master-side display, and
control a left-eye image and a right-eye image forming a medical image so as to be displayed on the slave-side display in a time-division manner in accordance with the synchronization signal acquired, wherein the master-side display displays a primary medical image and the slave-side display displays at least one of the primary medical image, a secondary medical image, and a modal image.

2. The medical-image display control device according to claim 1, wherein the circuitry is further configured to delay display of a left-eye image and a right-eye image forming a medical image on the slave-side display in accordance with the synchronization signal, thereby synchronizing timing in which the left-eye image and the right-eye image are displayed with timing in which the other device causes the master-side display to display a left-eye image and a right-eye image forming a medical image.

3. The medical-image display control device according to claim 1, comprising the slave-side display.

4. The medical-image display control device according to claim 1, wherein the circuitry is configured to feed the acquired synchronization signal to a device including the slave-side display, thereby controlling a left-eye image and a right-eye image forming a medical image so as to be displayed on the slave-side display in a time-division manner in accordance with the synchronization signal.

5. The medical-image display control device according to claim 1, wherein the circuitry is configured to transmit, to another device, a synchronization signal that corresponds to timing in which a left-eye image and a right-eye image forming a medical image are displayed on the slave-side display in a time-division manner according to a predetermined condition.

6. A medical-image display device comprising:
a display; and
circuitry configured to control a left-eye image and a right-eye image forming a primary medical image so as to be displayed on the display in a time-division manner; and
transmit a synchronization signal that corresponds to timing in which a left-eye image and a right-eye image forming a medical image are displayed on the display to another display to display at least one of the primary medical image, a secondary medical image, and a modal image in a time-division manner in accordance with the synchronization signal.

7. A medical-information processing system comprising a plurality of devices, wherein
a device among the plurality of devices that is to display a primary medical image operates as a master device, and another device that is to display an image other than the primary medical device operates as a slave device,
the master device
controls a left-eye image and a right-eye image forming a medical image so as to be displayed on a master-side display in a time-division manner, and
transmits a synchronization signal that corresponds to timing in which the left-eye image and the right-eye image are displayed, and
the slave device acquires the synchronization signal and controls a left-eye image and a right-eye image forming a medical image so as to be displayed in a time-division manner on a slave-side display in accordance with the synchronization signal.

8. The medical-information processing system according to claim 7, wherein
the master device includes:
the master-side display; and
master circuitry configured to
control a left-eye image and a right-eye image forming a medical image so as to be displayed on the master-side display in a time-division manner; and
transmit the synchronization signal, and
the slave device includes:
slave circuitry configured to
acquire the synchronization signal from the mastery circuitry; and
control a left-eye image and a right-eye image forming a medical image so as to be displayed on the slave-side display in a time-division manner in accordance with the synchronization signal.

9. The medical-information processing system according to claim 7, wherein the master device is selectively switched to any device among the plurality of devices according to a predetermined condition.

10. The medical-information processing system according to claim 9, wherein the master device is dynamically switched in accordance with a display that is an output source of a medical image to be viewed by a predetermined viewer.

11. The medical-information processing system according to claim 9, wherein, when a device operating as the slave device is switched so as to operate as the master device, a device having operated as the master device before the switching operates as a slave device after the switching.

12. The medical-information processing system according to claim 7, comprising shutter glasses including a left-eye shutter and a right-eye shutter, wherein
the shutter glasses control each of the left-eye shutter and the right-eye shutter so as to be opened and closed in accordance with the synchronization signal.

13. The medical-information processing system according to claim 7, comprising a camera that captures an image of a diseased site, wherein
the master circuitry is configured to cause the master-side display to display a left-eye image and a right-eye image forming a medical image that corresponds to an image of the diseased site in a time-division manner as the primary medical image.

14. A medical-image display control method causing a computer to execute:
controlling a medical image so as to be displayed on a slave-side display;
acquiring, from another device including a master-side display different from the slave-side display, a synchronization signal that corresponds to timing in which the other device displays a left-eye image and a right-eye image forming a medical image on the master-side display; and
displaying a left-eye image and a right-eye image forming a medical image so as to be displayed on the slave-side display in a time-division manner in accordance with the synchronization signal acquired, wherein the master-side display displays a primary medical image and the slave-side display displays at least one of the primary medical image, a secondary medical image, and a modal image.

15. A medical-image display control method causing a computer to execute:
controlling a left-eye image and a right-eye image forming a primary medical image so as to be displayed on a predetermined display in a time-division manner; and
transmitting a synchronization signal that corresponds to timing in which a left-eye image and a right-eye image forming the primary medical image are displayed on the display to another display to display at least one of the primary medical image, a secondary medical image, and a modal image in a time-division manner in accordance with the synchronization signal.

16. The medical-image display control method according to claim 15, wherein the primary medical image is an image of a surgical site.

17. The medical-image display control device according to claim 1, wherein the primary medical image is an image of a surgical site.

18. The medical-image display device according to claim 6, wherein the primary medical image is an image of a surgical site.

19. The medical-information processing system according to claim 7, wherein the primary medical image is an image of a surgical site.

20. The medical-image display control method according to claim 14, wherein the primary medical image is an image of a surgical site.

* * * * *